(12) United States Patent
Gerbec et al.

(10) Patent No.: US 8,109,973 B2
(45) Date of Patent: Feb. 7, 2012

(54) METHOD FOR DYNAMIC VERTEBRAL STABILIZATION

(75) Inventors: Daniel E. Gerbec, Logan, UT (US); T. Wade Fallin, Hyde Park, UT (US)

(73) Assignee: Stryker Spine (FR)

(*) Notice: Subject to any disclaimer, the term of this patent is extended or adjusted under 35 U.S.C. 154(b) by 1298 days.

(21) Appl. No.: 11/589,512

(22) Filed: Oct. 30, 2006

(65) Prior Publication Data

US 2007/0135815 A1    Jun. 14, 2007

Related U.S. Application Data

(60) Provisional application No. 60/732,265, filed on Oct. 31, 2005.

(51) Int. Cl.
*A61B 17/70* (2006.01)
(52) U.S. Cl. ..................................................... 606/255
(58) Field of Classification Search ........... 606/264–279
See application file for complete search history.

(56) References Cited

U.S. PATENT DOCUMENTS

| | | | |
|---|---|---|---|
| 3,599,245 A * | 8/1971 | Blatchford | 623/45 |
| 4,369,769 A | 1/1983 | Edwards | |
| 4,743,260 A | 5/1988 | Burton | |
| 4,947,835 A * | 8/1990 | Hepburn et al. | 602/16 |
| 5,034,011 A | 7/1991 | Howland | |
| 5,036,837 A * | 8/1991 | Mitchell et al. | 606/241 |
| 5,092,866 A | 3/1992 | Breard et al. | |
| 5,180,393 A | 1/1993 | Commarmond et al. | |
| 5,236,460 A * | 8/1993 | Barber | 623/17.15 |
| 5,282,863 A | 2/1994 | Burton | |
| 5,375,823 A | 12/1994 | Navas et al. | |
| 5,415,661 A | 5/1995 | Holmes | |
| 5,480,401 A | 1/1996 | Navas et al. | |
| 5,540,688 A | 7/1996 | Navas et al. | |
| 5,562,737 A | 10/1996 | Graf et al. | |
| 5,609,634 A | 3/1997 | Voydeville et al. | |

(Continued)

FOREIGN PATENT DOCUMENTS

DE         2821678         11/1979

(Continued)

OTHER PUBLICATIONS

U.S. Appl. No. 12/070,256.

(Continued)

*Primary Examiner* — Eduardo C Robert
*Assistant Examiner* — Mary Hoffman
(74) *Attorney, Agent, or Firm* — Lerner, David, Littenberg, Krumholz & Mentlik, LLP

(57) ABSTRACT

An intervertebral stabilization device and method is disclosed. The device preferably includes a planar spring enclosed within a housing. The housing is joined to an articulation component at either end, and the articulation components have couplings connectable to anchoring components which are securable to adjacent vertebrae. The planar spring can flex and retract providing relative motion between the adjacent vertebrae. The articulation components are ball and socket joints which allow the entire assembly to flexibly follow the curvature of the spine. A fusion rod with articulation components and couplings at either end may be substituted for the spring device. The couplings enable interchangeability between a fusion rod assembly and spring assembly, so that dynamic stabilization can occur at one vertebral level and fusion at the adjacent vertebral level. An overhung spring assembly with a sideways displaced housing which allows for a shorter pedicle to pedicle displacement is also disclosed.

15 Claims, 29 Drawing Sheets

U.S. PATENT DOCUMENTS

| | | |
|---|---|---|
| 5,645,599 A | 7/1997 | Samani et al. |
| 5,672,175 A * | 9/1997 | Martin .................... 606/86 A |
| 5,704,936 A | 1/1998 | Mazel et al. |
| 5,725,582 A | 3/1998 | Bevan et al. |
| 5,733,284 A * | 3/1998 | Martin .................... 606/248 |
| 5,749,873 A | 5/1998 | Fairley et al. |
| 5,836,948 A | 11/1998 | Zucherman et al. |
| 5,860,977 A | 1/1999 | Zucherman et al. |
| 5,876,404 A | 3/1999 | Zucherman et al. |
| RE36,221 E | 6/1999 | Breard et al. |
| 5,934,354 A | 8/1999 | Price et al. |
| 5,961,516 A | 10/1999 | Graf et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,176,881 B1 | 1/2001 | Schar et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,241,730 B1 | 6/2001 | Alby et al. |
| 6,267,764 B1 | 7/2001 | Elberg |
| 6,280,444 B1 | 8/2001 | Zucherman et al. |
| 6,290,700 B1 | 9/2001 | Schmotzer et al. |
| 6,293,949 B1 | 9/2001 | Justis et al. |
| 6,296,644 B1 | 10/2001 | Saurat et al. |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,423,065 B2 | 7/2002 | Ferree |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,582,400 B1 * | 6/2003 | Hawk et al. ............... 604/164.01 |
| 6,582,433 B2 | 6/2003 | Yun |
| 6,585,769 B1 | 7/2003 | Muhanna et al. |
| 6,616,669 B2 | 9/2003 | Ogilvie et al. |
| 6,626,944 B1 | 9/2003 | Taylor et al. |
| 6,652,527 B2 | 11/2003 | Zucherman et al. |
| 6,652,534 B2 | 11/2003 | Zucherman et al. |
| 6,652,585 B2 | 11/2003 | Lange |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,761,719 B2 | 7/2004 | Justis et al. |
| 6,761,720 B1 | 7/2004 | Senegas et al. |
| 6,770,094 B2 * | 8/2004 | Fehling et al. ............. 623/17.13 |
| 6,783,527 B2 | 8/2004 | Drewry et al. |
| 6,796,983 B1 | 9/2004 | Zucherman et al. |
| 6,802,844 B2 | 10/2004 | Ferree |
| 6,835,205 B2 | 12/2004 | Atkinson et al. |
| 6,835,207 B2 | 12/2004 | Zacouto et al. |
| 7,022,138 B2 | 4/2006 | Mashburn |
| 7,029,475 B2 | 4/2006 | Panjabi |
| 7,291,150 B2 * | 11/2007 | Graf ............................ 606/86 A |
| 7,476,238 B2 * | 1/2009 | Panjabi ........................ 606/257 |
| 7,879,074 B2 | 2/2011 | Kwak et al. |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2002/0091446 A1 | 7/2002 | Zucherman et al. |
| 2002/0116000 A1 | 8/2002 | Zucherman et al. |
| 2002/0133155 A1 | 9/2002 | Ferree |
| 2002/0143331 A1 | 10/2002 | Zucherman et al. |
| 2002/0151978 A1 | 10/2002 | Zacouto et al. |
| 2002/0183746 A1 | 12/2002 | Zucherman et al. |
| 2003/0009226 A1 | 1/2003 | Graf |
| 2003/0065330 A1 | 4/2003 | Zucherman et al. |
| 2003/0109880 A1 | 6/2003 | Shirado et al. |
| 2003/0171749 A1 | 9/2003 | Le Couedic et al. |
| 2003/0191470 A1 | 10/2003 | Ritland |
| 2003/0220642 A1 | 11/2003 | Freudiger |
| 2003/0220643 A1 | 11/2003 | Ferree |
| 2004/0002708 A1 | 1/2004 | Ritland |
| 2004/0006341 A1 | 1/2004 | Shaolian et al. |
| 2004/0006343 A1 * | 1/2004 | Sevrain ........................... 606/61 |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0143264 A1 | 7/2004 | McAfee |
| 2004/0147928 A1 | 7/2004 | Landry et al. |
| 2004/0153071 A1 | 8/2004 | Zucherman et al. |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0215191 A1 | 10/2004 | Kitchen |
| 2004/0220568 A1 | 11/2004 | Zucherman et al. |
| 2004/0225289 A1 | 11/2004 | Biedermann et al. |
| 2004/0236327 A1 * | 11/2004 | Paul et al. ........................ 606/61 |
| 2004/0236328 A1 | 11/2004 | Paul et al. |
| 2004/0236329 A1 | 11/2004 | Panjabi |
| 2004/0236343 A1 | 11/2004 | Taylor et al. |
| 2004/0243239 A1 | 12/2004 | Taylor |
| 2004/0267260 A1 | 12/2004 | Mack et al. |
| 2005/0010293 A1 | 1/2005 | Zucherman et al. |
| 2005/0010298 A1 | 1/2005 | Zucherman et al. |
| 2005/0033295 A1 | 2/2005 | Wisnewski |
| 2005/0049708 A1 | 3/2005 | Atkinson et al. |
| 2005/0056979 A1 | 3/2005 | Studer et al. |
| 2005/0065514 A1 | 3/2005 | Studer |
| 2005/0065515 A1 | 3/2005 | Jahng |
| 2005/0065516 A1 | 3/2005 | Jahng |
| 2005/0071006 A1 | 3/2005 | Kirschman ................. 623/17.11 |
| 2005/0085815 A1 | 4/2005 | Harms et al. |
| 2005/0090822 A1 * | 4/2005 | DiPoto ............................ 606/61 |
| 2005/0113927 A1 * | 5/2005 | Malek ........................ 623/17.16 |
| 2005/0141405 A1 | 6/2005 | Ootera et al. |
| 2005/0143737 A1 | 6/2005 | Pafford et al. |
| 2005/0143823 A1 | 6/2005 | Boyd et al. |
| 2005/0154390 A1 | 7/2005 | Biedermann et al. |
| 2005/0171543 A1 * | 8/2005 | Timm et al. ...................... 606/61 |
| 2005/0177156 A1 | 8/2005 | Timm et al. |
| 2005/0182400 A1 | 8/2005 | White |
| 2005/0182401 A1 | 8/2005 | Timm et al. |
| 2005/0203519 A1 | 9/2005 | Harms et al. |
| 2005/0222569 A1 | 10/2005 | Panjabi |
| 2005/0245930 A1 | 11/2005 | Timm et al. |
| 2005/0261682 A1 | 11/2005 | Ferree |
| 2005/0267485 A1 * | 12/2005 | Cordes et al. ..................... 606/88 |
| 2005/0288670 A1 | 12/2005 | Panjabi et al. |
| 2006/0009767 A1 * | 1/2006 | Kiester ............................ 606/61 |
| 2006/0015100 A1 | 1/2006 | Panjabi et al. |
| 2006/0036240 A1 | 2/2006 | Colleran et al. |
| 2006/0058792 A1 * | 3/2006 | Hynes ............................ 606/61 |
| 2006/0064090 A1 | 3/2006 | Park |
| 2006/0084988 A1 * | 4/2006 | Kim ................................ 606/61 |
| 2006/0085074 A1 * | 4/2006 | Raiszadeh ................. 623/17.12 |
| 2006/0155279 A1 * | 7/2006 | Ogilvie ........................... 606/61 |
| 2006/0189983 A1 | 8/2006 | Fallin et al. |
| 2006/0189984 A1 * | 8/2006 | Fallin et al. ..................... 606/61 |
| 2006/0235398 A1 * | 10/2006 | Farris et al. ..................... 606/69 |
| 2007/0016204 A1 * | 1/2007 | Martinez et al. ................ 606/69 |
| 2007/0173818 A1 * | 7/2007 | Hestad et al. ................... 606/61 |
| 2008/0177319 A1 * | 7/2008 | Schwab ........................ 606/257 |

| | | | | | | |
|---|---|---|---|---|---|---|
| 2008/0195156 | A1* | 8/2008 | Ainsworth et al. ............ 606/279 | WO | 01/64144 | 9/2001 |
| 2008/0208260 | A1* | 8/2008 | Truckai et al. ................ 606/280 | WO | 01/91657 | 12/2001 |
| 2010/0114318 | A1* | 5/2010 | Gittings et al. ............ 623/17.12 | WO | 01/91658 | 12/2001 |

FOREIGN PATENT DOCUMENTS

| | | |
|---|---|---|
| DE | 94 19 900 U1 | 4/1996 |
| DE | 10320417 | 12/2004 |
| EP | 322334 | 6/1989 |
| EP | 669109 | 8/1995 |
| EP | 0 677 277 | 10/1995 |
| EP | 768843 | 4/1997 |
| EP | 1239785 | 9/2002 |
| EP | 1343424 | 9/2003 |
| EP | 1399078 | 3/2004 |
| FR | 2 680 461 A1 | 2/1993 |
| FR | 2 704 137 | 10/1994 |
| FR | 2 717 370 | 9/1995 |
| FR | 2 738 143 | 3/1997 |
| FR | 2 778 089 A1 | 11/1999 |
| FR | 2 799 949 | 4/2001 |
| FR | 2 809 304 | 11/2001 |
| FR | 2 810 533 A1 | 12/2001 |
| FR | 2 843 538 | 2/2004 |
| GB | 2382304 | 5/2003 |
| JP | 06-285100 * | 10/1994 |
| JP | 07-289562 * | 11/1995 |
| JP | 10277070 | 10/1998 |
| WO | 94/21185 | 9/1994 |
| WO | 95/05783 | 3/1995 |
| WO | 97/32533 | 9/1997 |
| WO | 98/22033 | 5/1998 |
| WO | 99/21500 | 5/1999 |
| WO | 99/21501 | 5/1999 |
| WO | 01/08574 A1 | 2/2001 |
| WO | 01/28442 | 4/2001 |
| WO | 01/45576 | 6/2001 |
| WO | 01/52758 A1 | 7/2001 |
| WO | 01/56481 | 8/2001 |
| WO | 01/95818 | 12/2001 |
| WO | 02/03882 | 1/2002 |
| WO | 02/07621 | 1/2002 |
| WO | 02/07622 | 1/2002 |
| WO | 02/07623 | 1/2002 |
| WO | 02/30336 | 4/2002 |
| WO | 02/051326 | 7/2002 |
| WO | 02/067792 | 9/2002 |
| WO | 02/067793 | 9/2002 |
| WO | 02/102259 | 12/2002 |
| WO | 03/015646 | 2/2003 |
| WO | 03/045262 | 6/2003 |
| WO | 03/077806 | 9/2003 |
| WO | 2004/024011 | 3/2004 |
| WO | 2004017817 | 3/2004 |
| WO | 2004019762 | 3/2004 |
| WO | 2004024010 | 3/2004 |
| WO | 2004032794 | 4/2004 |
| WO | 2004039239 | 5/2004 |
| WO | 2004039243 | 5/2004 |
| WO | 2004041066 | 5/2004 |
| WO | 2004073533 | 9/2004 |
| WO | 2004098423 | 11/2004 |
| WO | 2004098452 | 11/2004 |
| WO | 2004105577 | 12/2004 |
| WO | 2004105580 | 12/2004 |
| WO | 2004110287 | 12/2004 |
| WO | 2005/030066 | 4/2005 |

OTHER PUBLICATIONS

U.S. Appl. No. 11/087,434.

U.S. Appl. No. 11/589,649.

* cited by examiner

METHOD FOR DYNAMIC VERTEBRAL STABILIZATION

CROSS REFERENCE TO RELATED APPLICATIONS

The present application claims the benefit of U.S. Provisional Patent Application No. 60/732,265 filed Oct. 31, 2005, the disclosure of which is hereby incorporated herein by reference.

BACKGROUND OF THE INVENTION

The present invention relates to orthopedic medicine, and more particularly to systems and methods for restricting relative motion between vertebrae.

Unfortunately millions of people experience back pain, and such is not only uncomfortable, but can be particularly debilitating. For example, many people who wish to participate in sports, manual labor, or even sedentary employment are unable to do so because of pains that arise from motion of or pressure on the spinal column. These pains are often caused by traumatic, inflammatory, metabolic, synovial, neoplastic and degenerative disorders of the spine.

In a normal spinal column, intervertebral discs that separate adjacent vertebrae from each other serve to provide stiffness that helps to restrain relative motion of the individual vertebrae in flexion, extension, axial rotation, and lateral bending. However, a damaged disc may provide inadequate stiffness along one or more modes of spinal motion. This inadequate stiffness may result in excessive relative vertebral motion when the spine is under a given load, as when the patient uses the muscles of the back. Such excessive relative motion may cause further damage to the disc, thereby causing back pain and ultimately, requiring replacement of the disc and/or other operations to decompress nerves affected by central, lateral or foraminal stenosis.

Heretofore, some stabilization devices have been proposed to restrict, but not entirely prevent, relative motion between adjacent vertebrae. These devices often contain linear springs that are too long to be easily positioned between adjacent vertebrae. Thus, they are often impossible to implant on motion segments where there is a short pedicle-to-pedicle displacement. Furthermore, known spinal implants typically have components that are either flexible, allowing limited relative motion between adjacent vertebrae, or rigid, providing fusion between vertebrae. Thus, they do not provide for interchangeability between flexible and rigid components. Accordingly, symptoms that would normally indicate stabilization and fusion of adjacent motion segments cannot be adequately treated, and vice versa. In other words, revision of an implant to provide fusion in place of stabilization is typically not feasible. Finally, many devices, when implanted in multiple levels along the spine, do not flexibly follow the natural curvature of the spine. Such devices may therefore cause discomfort, or restrict spinal motion in an unpredictable and unnatural manner.

Therefore, there exists a need for a system and method which corrects the above-noted shortcomings and allows for dynamic vertebral stabilization to restore normal movement and comfort to a patient.

SUMMARY OF THE INVENTION

A first aspect of the present invention is a stabilization system for controlling relative motion between a first vertebra and a second vertebra. In accordance with this first aspect, on embodiment stabilization system may include a first stabilizer having a first coupling adapted to be attached to a first anchoring member, a second coupling adapted to be attached to a second anchoring member and a resilient member configured to be coupled to the first and second couplings to transmit resilient force between the first and second couplings, the resilient member including a planar spring, wherein at least a portion of the planar spring flexes out-of-plane in response to relative motion between the vertebrae.

In other embodiments of the first aspect, the first stabilizer may further include a casing including a hollow first member and a hollow second member, wherein the resilient member is positioned within a cavity defined by engagement of the first and second hollow members. The resilient member is may also be positioned inside the casing such that the casing limits relative motion of the vertebrae by limiting deflection of the planar spring. The system may also include the first anchoring member and the second anchoring member, where the first and second anchoring members include a yoke polyaxially coupled to a fixation member implantable in a portion of either the first or second vertebra. The system may also include a first rigid connector including first and second couplings adapted to be attached to one of the first and second anchoring members, wherein the couplings are substantially rigidly connected together. In other embodiments, the path followed by the planar spring may be generally spiral-shaped, wherein the planar spring includes a central portion attached to the first coupling and a peripheral portion attached to the second coupling. The first stabilizer may further include a first articulation component configured to articulate to permit polyaxial relative rotation between one of the first or second couplings. The first articulation component may include a semispherical surface and a socket within which the semispherical surface is rotatable to permit polyaxial motion between the resilient member and the first anchoring member. The resilient member may be coupled to the first and second couplings such that the resilient member is able to urge the first and second couplings to move closer together and is also able to urge the couplings to move further apart.

The stabilization system may include a second component comprising a third coupling and a fourth coupling, wherein the third coupling is adapted to be attached to the first anchoring member such that the first anchoring member is capable of simultaneously retaining the first and third couplings. The second component may be a rigid connector, wherein the third and fourth couplings are substantially rigidly connected together, or the second component may be a second stabilizer comprising a second resilient member configured to exert resilient force between the third and fourth couplings.

Another aspect of the present invention is another stabilization system for controlling relative motion between a first vertebra and a second vertebra. In accordance with this second aspect, the stabilization system may include a first stabilizer having a first coupling adapted to rest within a yoke of a first anchoring member, a second coupling adapted to rest within a yoke of a second anchoring member, a resilient member coupled to the first and second couplings to transmit resilient force between the first and second couplings, the resilient member including a planar spring, wherein at least a portion of the planar spring flexes out-of-plane in response to relative motion between the vertebrae and a first articulation component configured to articulate to permit relative rotation between the first stabilizer and one of the first or second couplings.

Still another aspect of the present invention is a stabilization system for controlling relative motion between a first vertebra and a second vertebra. The stabilization system according to this aspect may include a first stabilizer having a first coupling adapted to be attached to a first anchoring member, a second coupling adapted to be attached to a second anchoring member, a resilient member configured to be coupled to the first and second couplings to transmit resilient force between the first and second couplings, the resilient member including a planar spring, wherein at least a portion of the planar spring flexes out-of-plane in response to relative motion between the vertebrae, a first articulation component configured to articulate to permit relative rotation between the first and second couplings and a first rigid connector including third and fourth couplings adapted to be attached to the first and second anchoring members, wherein the third and fourth couplings are substantially rigidly connected together.

Yet another aspect of the present invention is a method for controlling relative motion between a first vertebra and a second vertebra. In accordance with this aspect, the method may include the steps of positioning a planar spring of a first stabilizer attaching a first coupling of the first stabilizer to the first vertebra and attaching a second coupling of the first stabilizer to the second vertebra, wherein, after attachment of the couplings to the vertebrae, the planar spring is positioned to transmit resilient force between the vertebrae via flexure of at least a portion of the planar spring out-of-plane.

Yet another aspect of the present invention is another method for controlling relative motion between a first vertebra and a second vertebra. In accordance with this aspect, the method may include selecting a component selected from the group consisting of a first stabilizer and a first rigid connector, wherein the first stabilizer comprises a first coupling, a second coupling adapted to be attached to a second anchoring member secured to the second vertebra, a resilient member configured to transmit resilient force between the first and second couplings, and a first articulation component configured to articulate to permit relative rotation between the first and second couplings, wherein the first rigid connector comprises a first coupling and a second coupling substantially rigidly connected to the first coupling, attaching a first coupling of the selected component to a first anchoring member secured to the first vertebra and attaching a second coupling of the selected component to a second anchoring member secured to the second vertebra.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

The present invention relates to systems and methods for stabilizing the relative motion of spinal vertebrae. Those of ordinary skill in the art will recognize that the following description is merely illustrative of the principles of the invention, which may be applied in various ways to provide many different alternative embodiments. This description is understandably set forth for the purpose of illustrating the general principles of this invention and is not meant to limit the inventive concepts in the appended claims.

Figure 1:
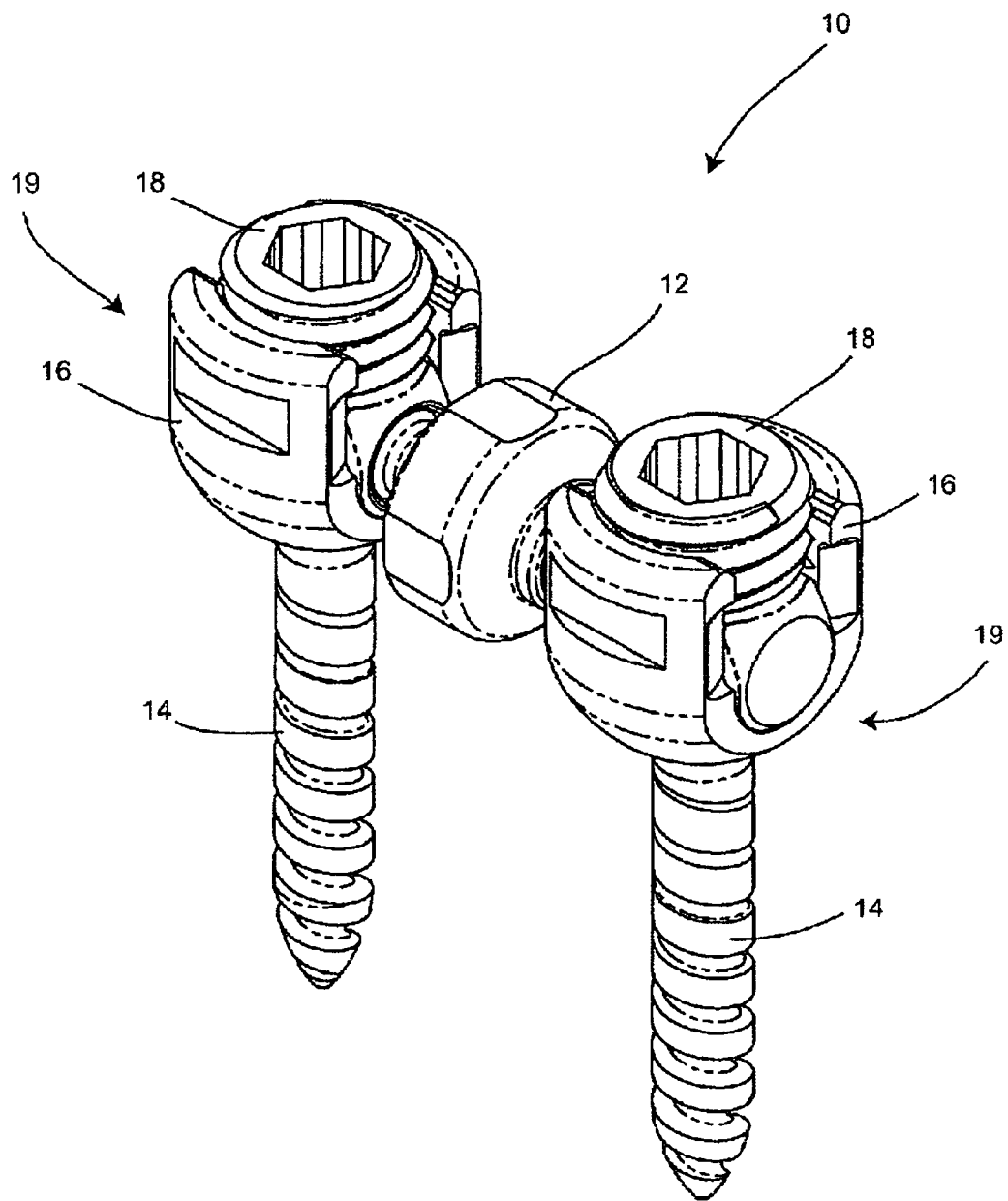
FIG. 1 is a perspective view of a dynamic stabilization assembly according to one embodiment of the invention.

Referring to FIG. 1, one embodiment of a single level dynamic stabilization system 10 is shown. The dynamic stabilization system 10 preferably includes a stabilizer 12, a pair of fixation members 14, a pair of yokes 16 securable to the fixation members 14, and a pair of set screws 18. The fixation members 14, yokes 16, and set screws 18 may be any of a variety of types known and available in the art, or may optionally be specially designed for operation with the stabilizer 12. Each fixation member 14 with its corresponding yoke 16 and set screw 18 provides an anchoring member 19 designed to anchor the stabilizer 12 to a pedicle or other portion of a vertebra (not shown). In the embodiments described and illustrated herein, the fixation members 14 are represented as pedicle screws. However, they could also be other types of screws fixed to other parts of the vertebrae, pins, clips, clamps, adhesive members, or any other device capable of anchoring the stabilizer to the vertebrae. Additionally, each yoke 16 may be unitarily formed with a fixation member 14 as illustrated herein, or each yoke 16 may be a separate entity and be polyaxially securable to a fixation member 14.

Figure 2:
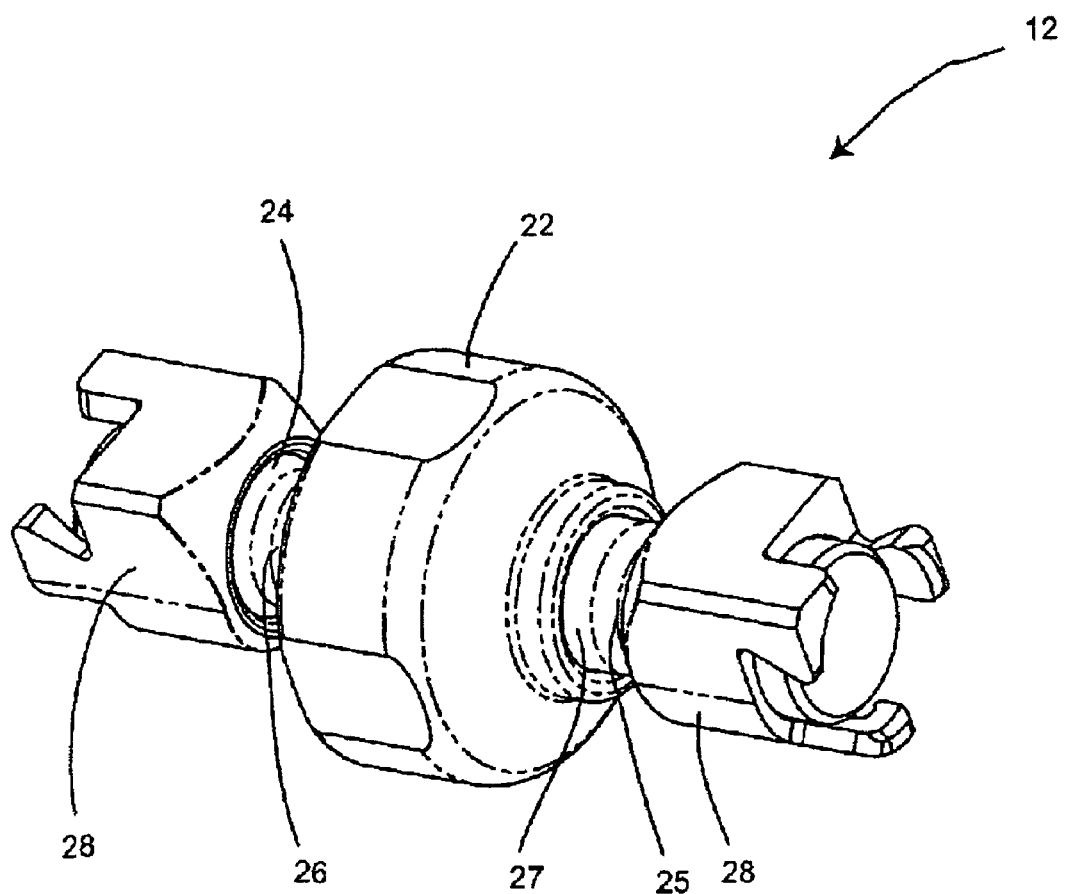
FIG. 2 is an enlarged perspective view a stabilizer of the dynamic stabilization assembly of FIG. 1.

The stabilizer 12 is illustrated alone in FIG. 2. As shown in that figure, stabilizer 12 includes a central spring casing 22, and a short arm 26 extending from the spring casing 22 on one side to an articulation component 24. On the opposite side, a longer arm 27 extends from the spring casing 22 to another articulation component 25. An end coupling 28 is also preferably located on the outside of each articulation component 24, 25. It is noted that the particular construction of stabilizer 12 depicted in FIG. 2 may vary. For example, the short arm 26 and longer arm 27 may be flipped to opposite sides.

Figure 3:
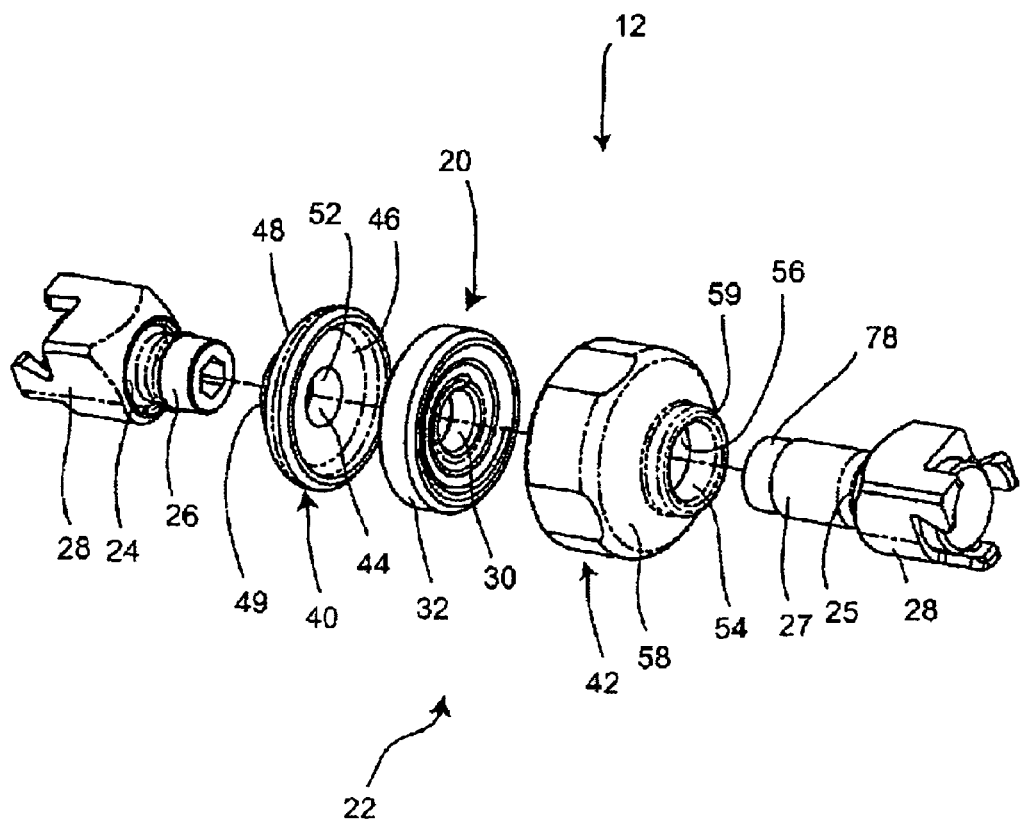
FIG. 3 is an exploded perspective view of the stabilizer of FIG. 2.

Referring to FIG. 3, an exploded view of the stabilizer 12 is shown, thereby illustrating the inner components of the stabilizer. For example, a planar spring 20 is shown encased within the spring casing 22. The planar spring 20 is preferably coiled in a planar spiral-like shape and has a threaded inner ring surface 30 and an outer ring surface 32. In addition, the spring casing 22 is made up of two concentric hollow members, an inner hollow member 40 and an outer hollow member 42, with the planar spring 20 being disposed within the inner hollow member 40. A circular bore 44 occupies the center of the inner hollow member 40, creating a round opening from an inside surface 46 to an outside surface 48. A protruding circular lip 49 may also surround the bore 44 where it exits the outside surface 48. An inner wall 52 of the lip 49 is preferably threaded. Similarly, a circular bore 54 occupies the center of the outer hollow member 42, creating a round opening from an inside surface 56 to an outside surface 58. A protruding circular lip 59 may also surround the bore 54 where it exits the outside surface 58.

Figure 4:
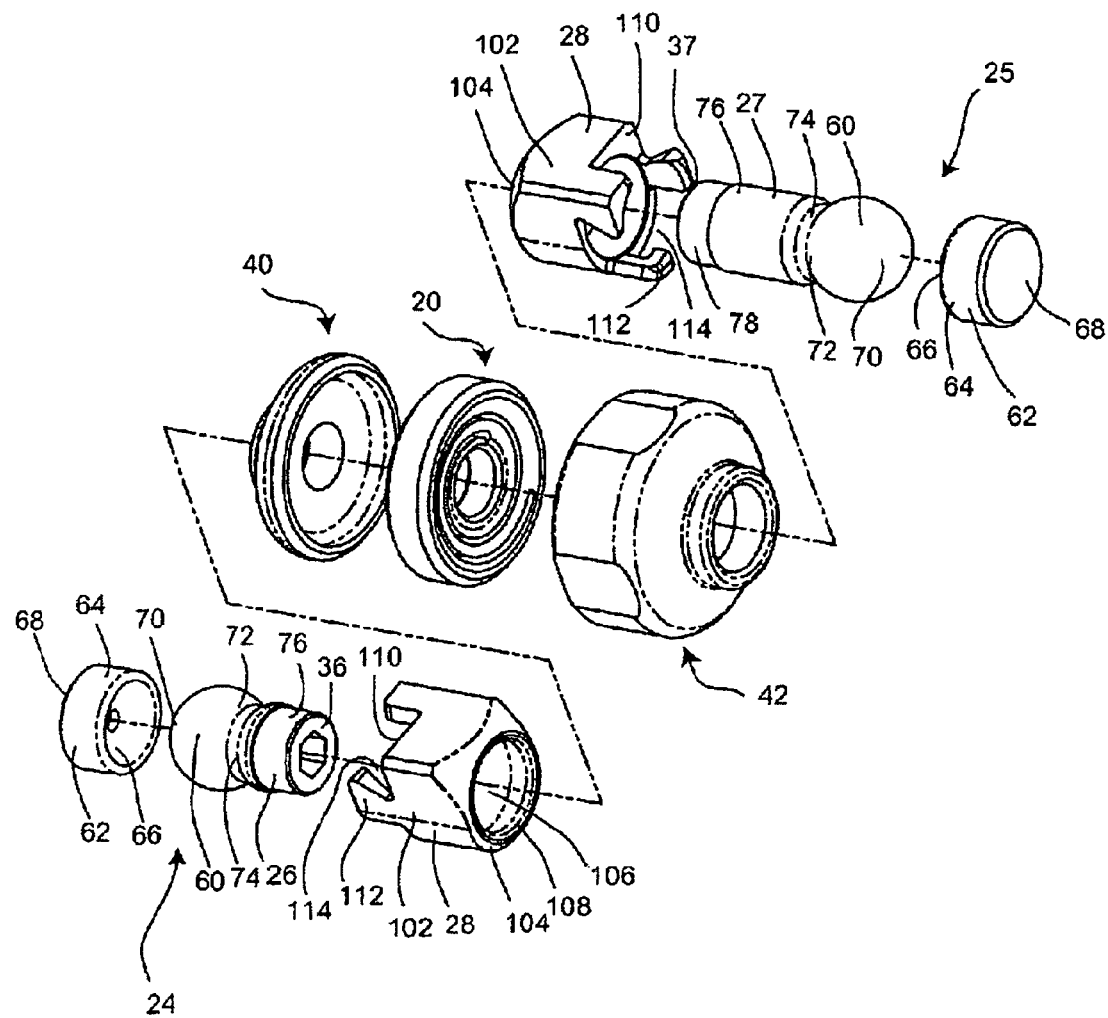
FIG. 4 is a further exploded perspective view of the stabilizer of FIG. 2.

Shown adjacent to the inner hollow member 40 is the short arm 26, which has a threaded outer surface 76 on the end closest to the inner hollow member 40. This end terminates at a flat end 36. Both surface 76 and flat end 36 are best shown in FIG. 4. On the opposite end of the short arm 26 is the articulation component 24, which terminates at the end coupling 28. Adjacent to the outer hollow member 42 is the long arm 27, which has a threaded terminal segment 78 on the end closest to the outer hollow member 42. The terminal segment terminates at a flat end 37 (best shown in FIG. 4). On the opposite end of the long arm 27 is the articulation component 25, which terminates at the end coupling 28.

When assembled, the short arm 26 fits inside the bore 44 of the inner hollow member 40. The threads on the outer surface 76 engage with the threads on the inner wall 52, thereby securing the pieces together. As mentioned above, the planar spring 20 fits inside the inner hollow member 40. In addition, the long arm 27 fits through the bore 54 of the outer hollow member 42, with the threaded terminal segment 78 engaging the threaded inner ring surface 30 of the planar spring 20. The inner hollow member 40 fits concentrically within the outer hollow member 42, with the planar spring 20 also being disposed inside. Inside of the hollow members 40, 42, the flat ends 36, 37 of the arms 26, 27 are preferably adjacent to one another but not touching.

When assembled with the hollow members 40, 42 and the arms 26, 27, the planar spring 20 can, if acted upon, flex out of the plane within which it is coiled. When the longer arm 27, to which the planar spring 20 is engaged, moves toward or away from the short arm 26, the spiral-like shape of the planar spring 20 preferably extends out of its plane. When the longer arm 27 returns to its original position, the planar spring 20 also preferably recoils back to its plane. During this extension and recoil, the inside surface 46 of the inner hollow member 40, and the inside surface 56 of the outer hollow member 42 act as barriers to limit the movement of the planar spring 20.

Use of the planar spring 20, as opposed to a longer helical spring, keeps the overall length of the stabilizer 12 relatively short. In alternative embodiments, a planar spring according to the invention need not have a spiral-like shape, but can rather be a cantilevered leaf spring, a flexible disc, or the like. Further, in other alternative embodiments, a planar spring need not be used; rather, a different type of spring or a conventional helical spring may be used.

FIG. 4 illustrates the articulation components 24, 25 in an exploded view. As is mentioned above, the articulation component 24 is located adjacent to and couples with the inner hollow member 40, and the articulation component 25 is located adjacent to and couples with the outer hollow member 42. Each articulation component 24, 25 preferably comprises a semispherical surface 60, a cup 62, which are both enclosed by the end coupling 28. The cup 62 is preferably dish shaped, with a cylindrical support wall 64 and two ends. On one end of the cup 62 is a depression 66, and on the opposite side of the cup 62 is a flat end 68. The semispherical surface 60 preferably has a round side 70 which rotatably fits inside the depression 66, so that each of the articulation components 24, 25 thus takes the form of a ball-and-socket joint. The opposite side of each semispherical surface 60 is a connecting side 72 which narrows into a neck 74. The neck 74 preferably widens into either the short arm 26 or the long arm 27, which extends away from the semispherical surface 60 on the opposite side from the round side 70. As is discussed above, the outer wall 76 of the short arm 26 is threaded, as is the terminal segment 78 of the long arm 27. In alternative embodiments, articulation components may be omitted, or may be formed by any other type of mechanical joints known in the art.

The end coupling 28 has a support wall 102 which forms the outer sides of the cup, and a base 104. A circular hole 106 occupies the center of the base 104, and where the edge of the hole 106 meets the base 104, a circular rim 108 preferably surrounds the hole 106. The inside diameter of the rim 108 is preferably less than the diameter of the semispherical surface 60 of the articulation components 24 and 25, so that when assembled the semispherical surface 60 will fit into the end coupling 28 but not be capable of passing through the hole 106. At the opposite end from the base 104, the support wall 102 terminates in a flat edge 110. Protruding from the edge 110 in the same plane as the support wall 102, such that they form continuations of the support wall 102, is a plurality of irregularly shaped teeth 112. Between each tooth 112 and the adjacent tooth is a notch 114.

When assembled, the round side 70 of each semispherical surface 60 rotatably rests in the depression 66 of the cup 62, and the arm 26 or 27 extends away from the joining side 72 of the semispherical surface 60. The generally cup-shaped end coupling 28 fits over each semispherical surface, arm and cup assembly. Each arm 26, 27 extends from its semispherical surface 60 through its respective hole 106. As described above, the arms then extend into the spring casing 22, the long arm 27 connecting to the planar spring 20 and the short arm 26 connecting to the inner hollow member 40. Rotation of either semispherical surface 60 results in movement of its arm 26, 27. When the short arm 26 moves, the flat end 37 of the opposite arm 27 may optionally contact the flat end 36 of the short arm 26 to acts as a stop to limit excessive movement. Similarly, when the long arm 27 moves, the flat end 36 of the opposite short arm 26 may stop excessive movement via contact with the flat end 37 of the long arm 27. Thus the articulation components 24, 25 secure the arms 26, 27 in a rotatable manner to the spring casing 22 to permit the stabilizer 12 to obtain a variable curvature.

Figure 5:
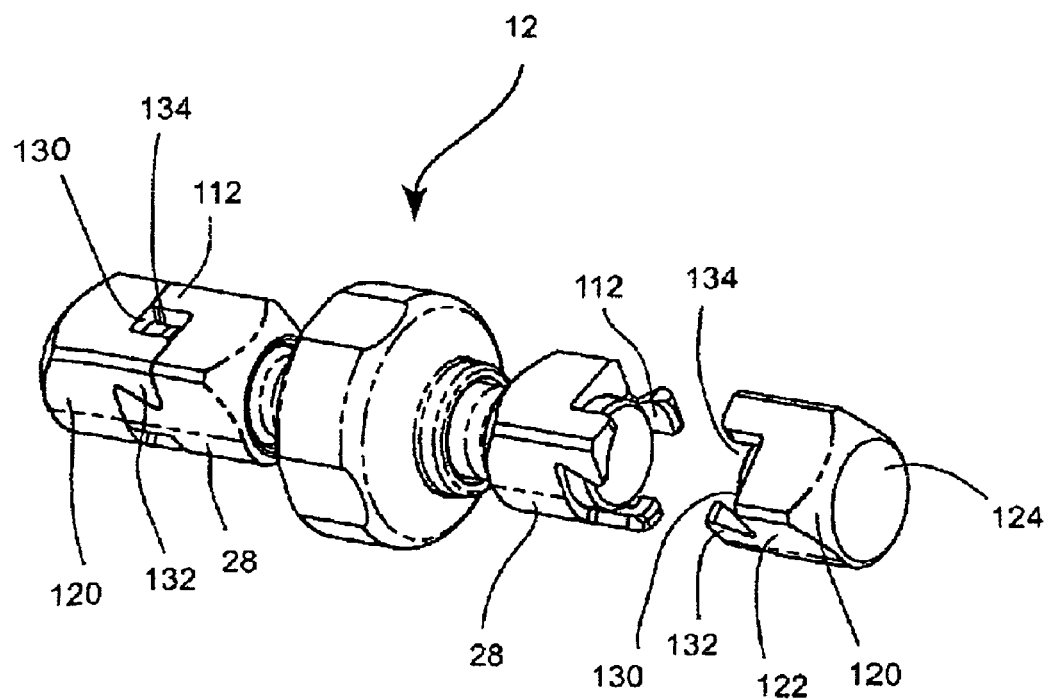
FIG. 5 is a partially exploded perspective view of the stabilizer of FIG. 2 having two end caps.

The assembled stabilizer 12 can be rotated into locking engagement with end caps or end couplings of other stabilizers for multi-level application. In fact, FIG. 5 illustrates one coupled stabilizer 12, having a coupled end cap 120 and an uncoupled end cap 120. Each end cap 120 preferably has a general cup-shape, much like each end coupling 28. Each end cap 120 preferably includes a support wall 122 which forms the outer sides of the cup, and a solid base 124 which forms the bottom of the cup. The inside diameter of the end cap 120 is sized to fit around either arm 26, 27. At an opposite end from the base 124, the support wall 122 terminates in a flat edge 130. Protruding from the edge 130 in the same plane as the support wall 122, such that they form continuations of the support wall 122, are a plurality of irregularly shaped teeth 132. Between each tooth 132 and the adjacent tooth is a notch 134.

Figure 6:
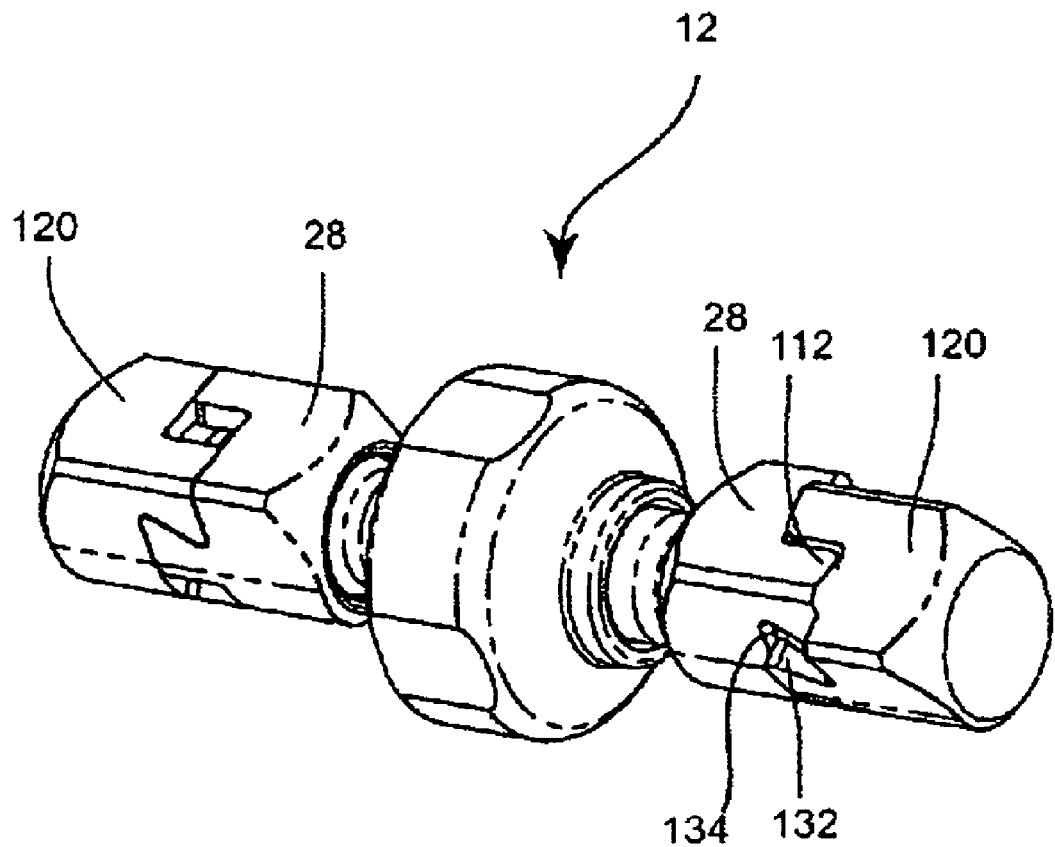
FIG. 6 is a perspective view of the stabilizer of FIG. 2, illustrating attachment of one end cap to an end coupling.
Figure 7:
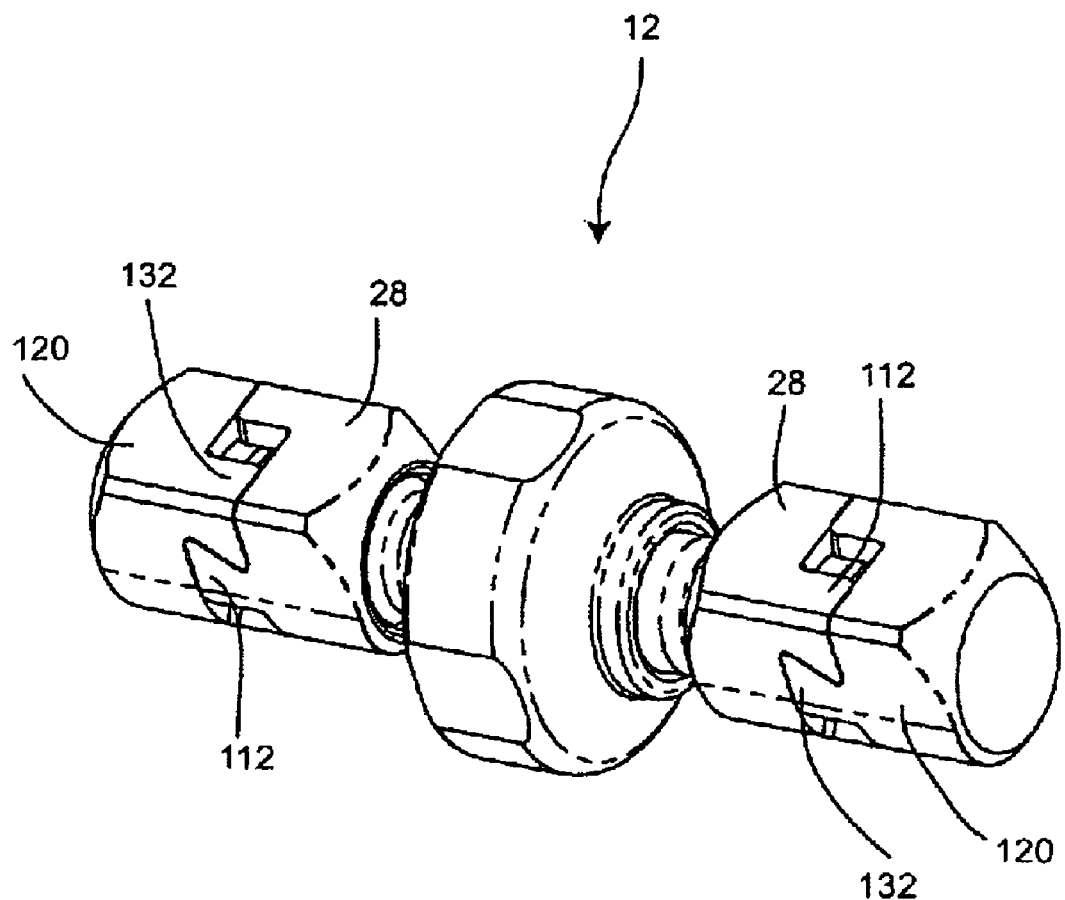
FIG. 7 is a perspective view of the stabilizer of FIG. 2 with attached end caps.

Referring to FIG. 6, an end cap 120 is illustrated in partial engagement to a stabilizer 12. When an end cap 120 is to be attached to an end coupling 28, the end cap 120 is preferably lined up with the end coupling 28 so that the teeth 112, 132 are pointed toward one another. The end cap 120 is then rotated and moved toward the end coupling 28 so that the teeth 132 fit into the notches 114, while the teeth 112 fit into the notches 134. When the teeth 112, 132 are fully seated in the notches 114, 134 such that the teeth 132 touch the edge 110 and the teeth 112 touch the edge 130, the end cap 120 is further rotated until the teeth 112, 132 interlock with each other and the end cap 120 is locked in place. A stabilizer 12 with two end caps 120 each fully engaged on opposite ends of the stabilizer 12 is depicted in FIG. 7. In this depiction, the end caps 120 have been fully rotated so that the teeth 132 of the end caps 120 are interlocked with the teeth 112 of both end couplings 28.

Figure 8:
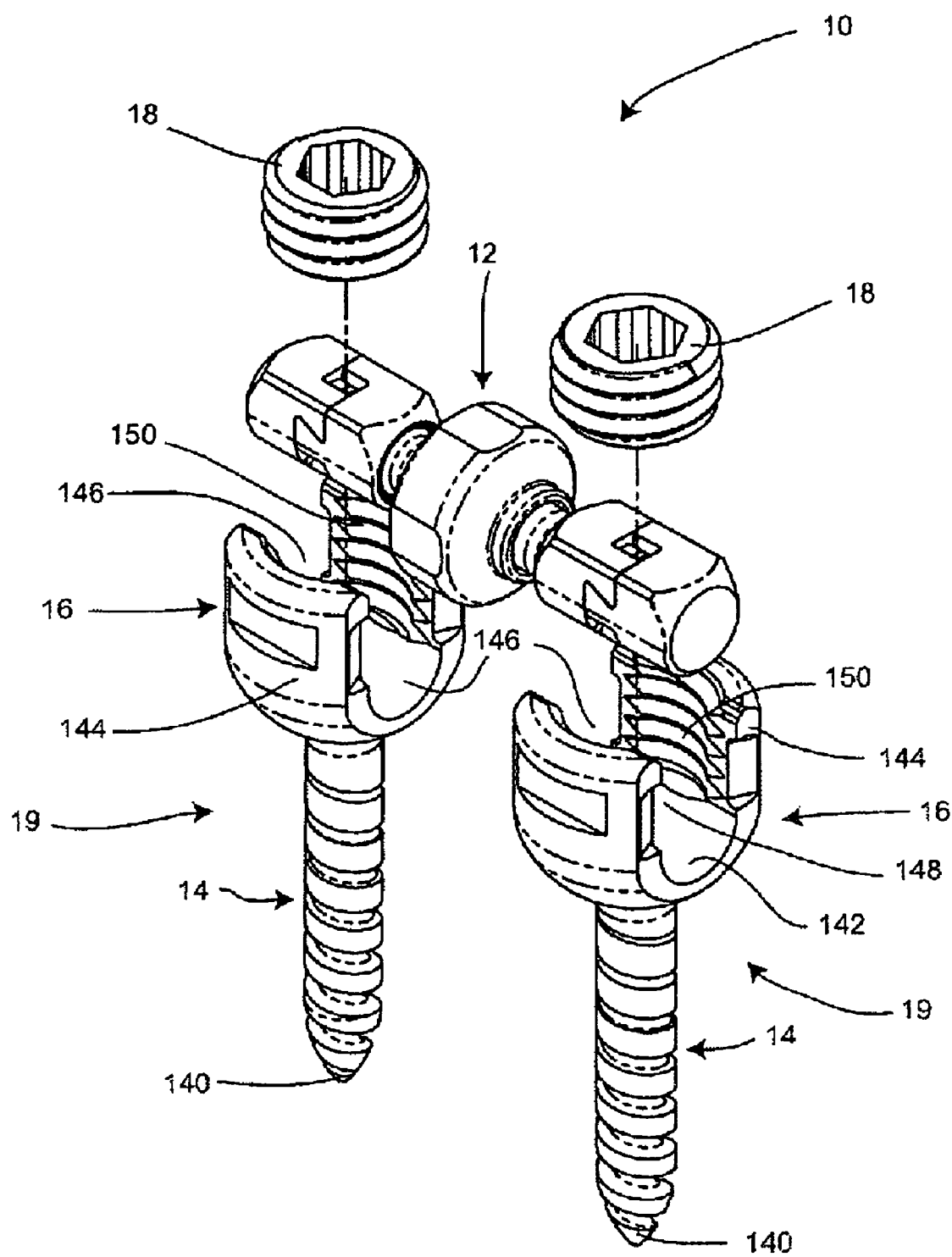
FIG. 8 is a partially exploded perspective view of the dynamic stabilization assembly of FIG. 1.

FIG. 8 shows an exploded view of the dynamic stabilization system 10 with a fully assembled stabilizer 12, two anchoring members 19 with yokes 16 and fixation members 14, and two set screws 18. In this design, each fixation member 14 preferably has a pointed end 140 which aids in screwing the member into a corresponding vertebra when implanted. The opposite end of the fixation member 14 is preferably unitarily formed with a U-shaped yoke 16, so that the bottom of the U is a head 142 of the fixation member 14. Each yoke 16 has two curved opposing support walls 144. Alternating between the support walls 144 are two opposing gaps 146, which form a cavity 148 therebetween that occupies the interior of the yoke 16. The inner surfaces 150 of the support walls 144 are also preferably threaded to engage a set screw 18.

According to the embodiment depicted, in use, the stabilizer 12 is inserted into the yokes 16 of two anchoring members 19 whose fixation members 14 have previously been anchored in the pedicles, or other portion, of the corresponding vertebrae. The stabilizer 12 is laid lengthwise into the yokes 16 such that the long axis of the stabilizer 12 is perpendicular to the long axes of the fixation members 14, and so that the spring casing 22 lies between the anchoring members 19. Each end coupling 28/end cap 120 pair preferably rests on the head 142 within the cavity 148. Each end cap preferably occupies the gaps 146, and the two articulation components 24, 25 lie adjacent to, but outside of, the two interior gaps 146.

The end couplings 28 and attached end caps 120 are preferably secured within the yokes 16 of the anchoring members 19 through the use of the set screws 18. One set screw 18 is screwed into the top of each yoke 16 so that its threads engage with the threaded inner surfaces 150 of the support walls 144. The set screws 18 are then tightened to hold the stabilizer 12 in place. As described above, an alternative embodiment of the invention includes yokes 16 which are separate entities from the fixation members 14, and are polyaxially securable to the fixation members 14. If such separate polyaxially securable yokes 16 are included, tightening of the set screws 18 may also press the end couplings 28 and end caps 120 against the heads 142 of the fixation members 14, thereby restricting further rotation of the polyaxially securable yokes 16 with respect to the fixation members 14 to secure the entire assembly. Those of ordinary skill in the art would readily recognize this operation.

Figure 9:
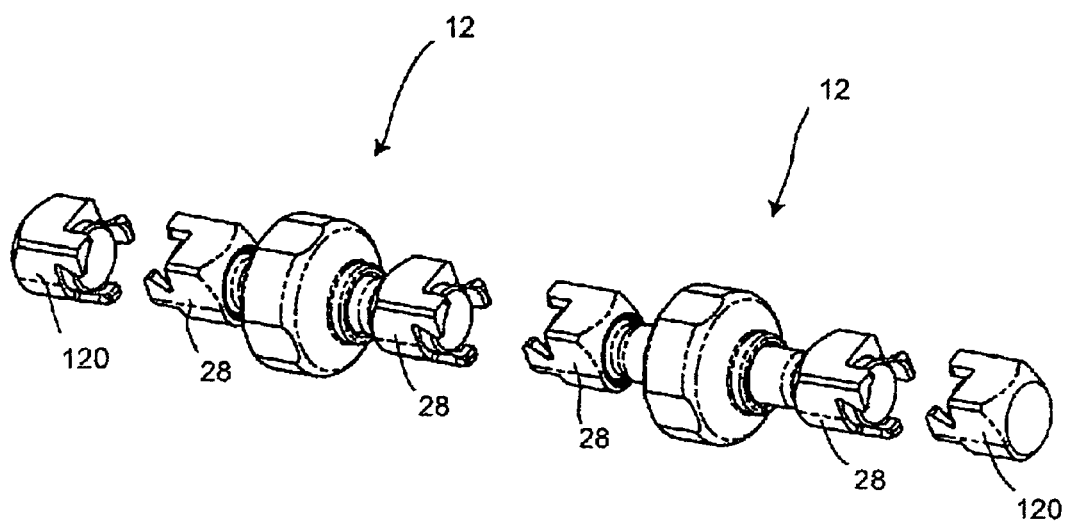
FIG. 9 is a perspective view of two of the stabilizers of FIG. 2, placed end to end, with two end caps being detached therefrom.
Figure 10:
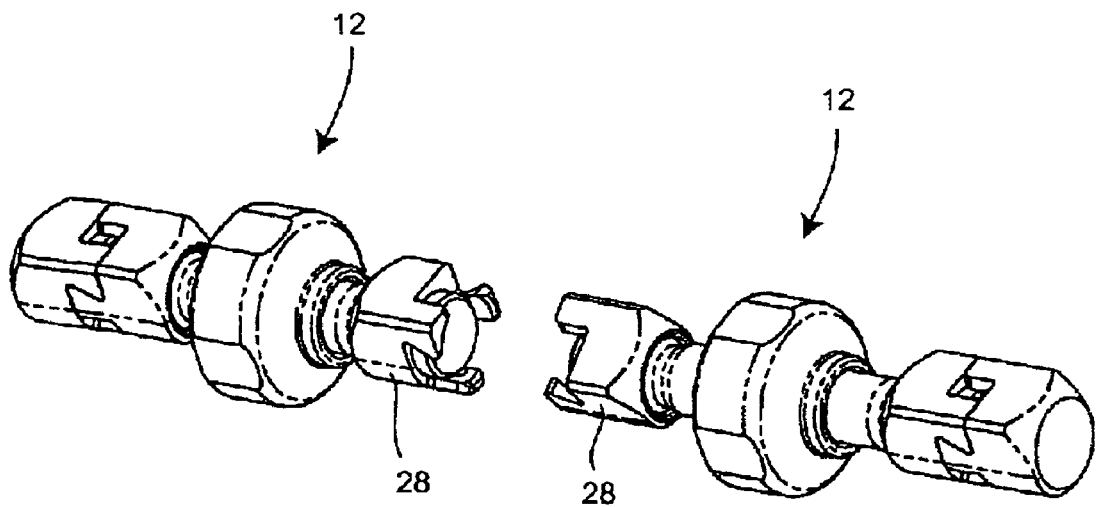
FIG. 10 is a perspective view of two of the stabilizers of FIG. 2, placed end to end, with two end caps being attached thereto.
Figure 11:
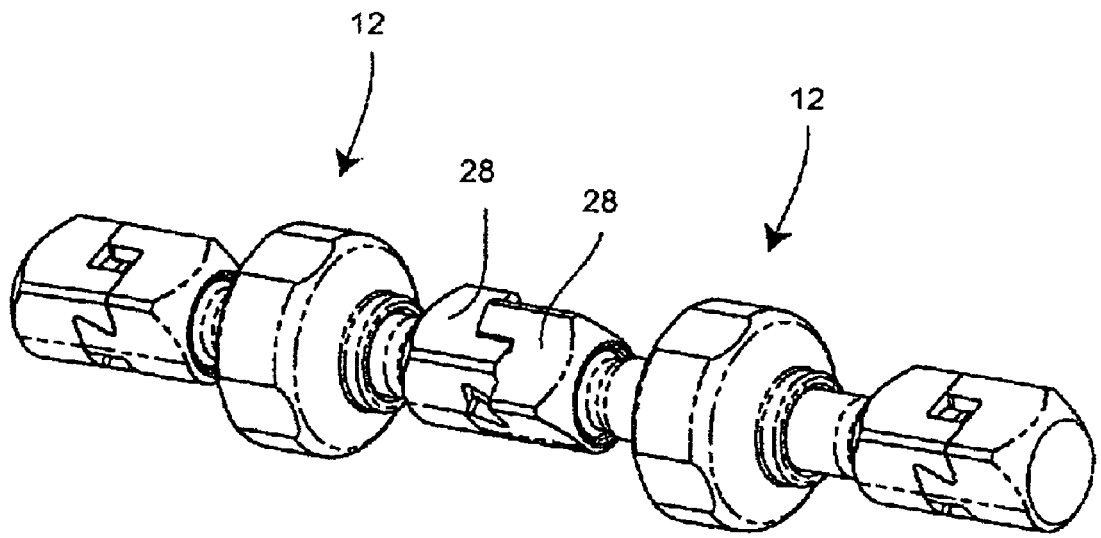
FIG. 11 is a perspective view of two stabilizers of FIG. 2, placed end to end, illustrating the coupling of the ends of the stabilizers to each other.
Figure 12:
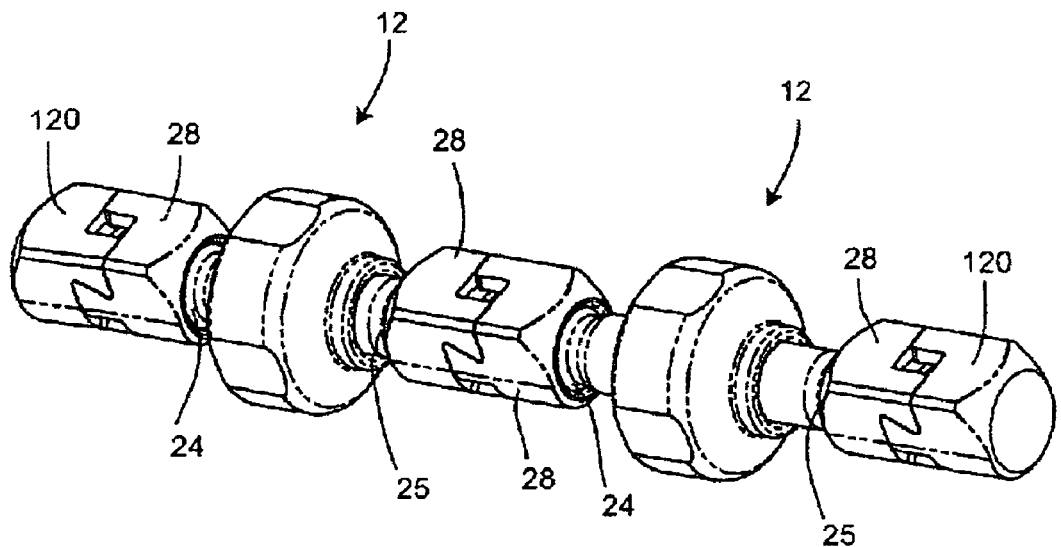
FIG. 12 is a perspective view of the stabilizer of FIG. 2, coupled end-to-end with a second stabilizer for multi-level vertebral stabilization.
Figure 13:
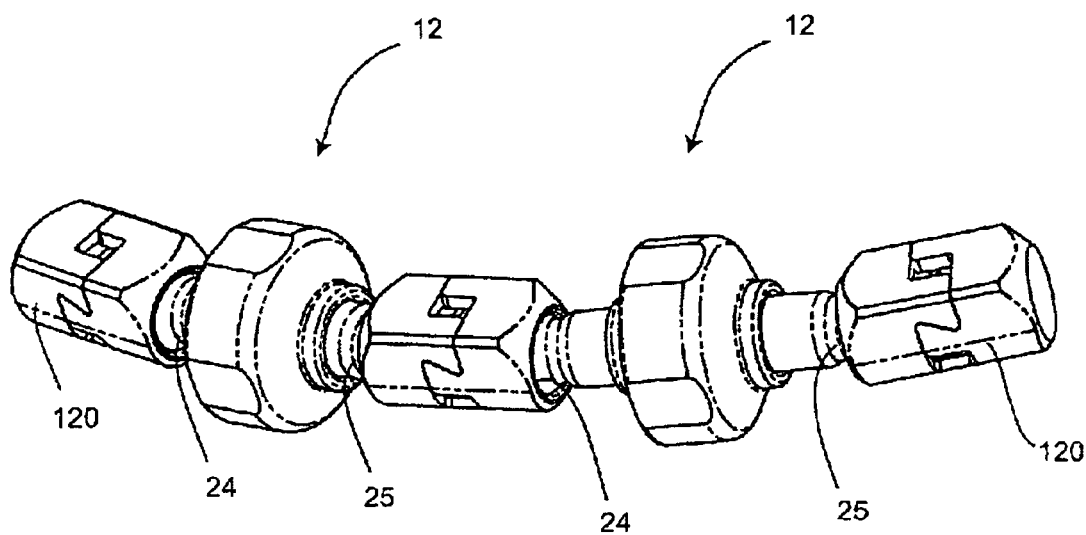
FIG. 13 is a perspective view of the two stabilizers of FIG. 12, illustrating how the articulation components may be used to provide an overall curvature to the assembled modules.

Referring to FIG. 9, two assembled stabilizers 12 are illustrated positioned end-to end with two end caps 120 positioned at the outer ends of the stabilizers 12. Two stabilizers 12 may be interlocked with each other end-to-end and implanted when it is desirable to stabilize the relative motion of three adjacent vertebrae. FIG. 10 depicts a similar assembly, with two stabilizers 12 being illustrated end-to-end, and one end cap 120 being secured to each outer end coupling 28 in a similar fashion to that previously depicted in FIG. 7. On the inner ends of each stabilizer 12, the teeth 112 of each end coupling 28 are aligned to fit into the notches 114 of the facing end coupling 28. FIG. 11 depicts the two stabilizers 12 in an end-to-end fashion and partially interlocked together. The teeth 112 of each facing end coupling 28 are in the notches 114 of the opposite end coupling 28, and the stabilizers 12 have been partially turned so that the teeth 112 are partially interlocked. In FIG. 12, the two stabilizers 12 are shown completely interlocked end-to-end. The end couplings 28 of the two stabilizers 12 are rotated into locking engagement with each other and an end cap 120 is locked onto each unoccupied external end coupling 28. The entire dynamic stabilization assembly has four articulation components 24, 25, which will permit considerable differentiation in orientation between the three fixation members 14 that would be used to attach the stabilizers 12 to three adjacent vertebrae (not shown). In fact, in FIG. 13, two interlocked stabilizers 12 are illustrated with the articulation components 24, 25 in an articulated position so that the stabilizers 12 no longer lie in a straight line, but instead the multi-level dynamic stabilization assembly approximates a curve. This enables the assembly to conform to the desired lordotic curve of the lower spine or to other spinal curvatures, such as those caused by or used to correct scoliosis. Additional levels can be added if desired.

Figure 14:
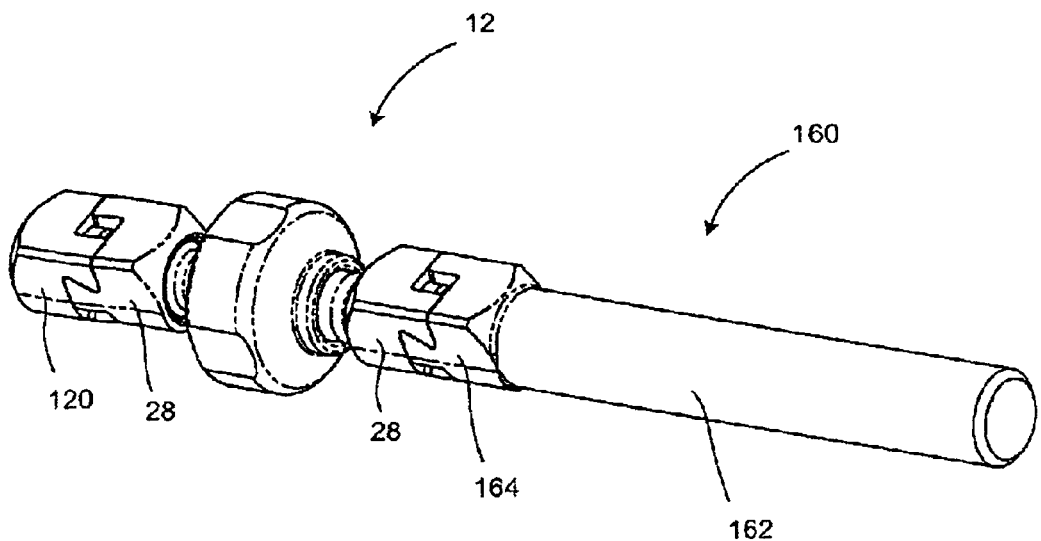
FIG. 14 is a perspective view of the stabilizer of FIG. 2, coupled end-to-end with a rigid connector and an end cap for single level vertebral joint stabilization with joint immobilization at an adjacent level.

Referring to FIG. 14, a stabilizer 12 is depicted secured end-to-end to a rigid connector 160 to provide dynamic stabilization across one level, and posterior immobilization and/or fusion across the adjacent level. The rigid connector 160 has a rod 162 and an end coupling 164. The end coupling 164 is toothed and notched so that it may engage the end coupling 28 on the stabilizer 12. This is not unlike the other couplings discussed above. In addition, and like that discussed above, the rod 162 may be secured in the yoke 16 of a fixation member 14 with a set screw 18. Similarly, the interlocked end coupling 164/end coupling 28 combination may be secured in the yoke 16 of an anchoring member 19 in a manner similar to the previously described securing of the end couplings and end caps. Additional rigid connectors 160 or stabilizers 12 with associated anchoring members 19 can be added if additional levels are desired.

Figure 15:
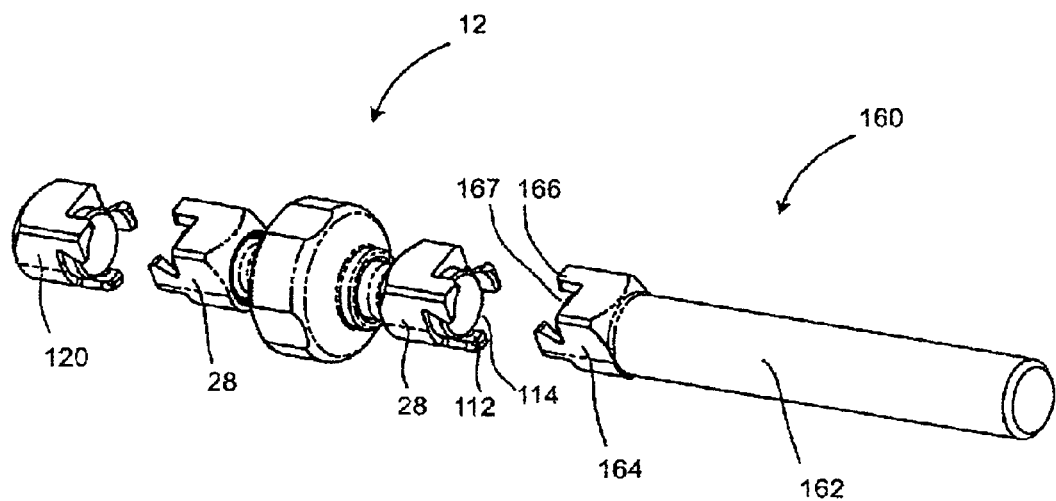
FIG. 15 is an exploded perspective view of the stabilizer and rigid connector of FIG. 14, illustrating the coupling of the stabilizer and the rigid connector to each other.
Figure 16:
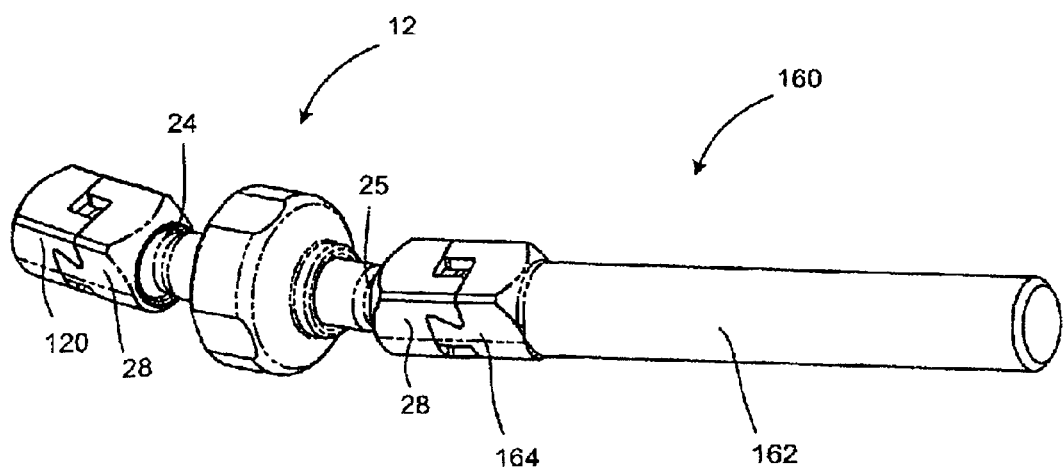
FIG. 16 is a perspective view of the stabilizer and rigid connector of FIG. 14, illustrating how the articulation components may be used to provide an overall curvature to the assembled modules.

FIG. 15 depicts an exploded view of the system depicted in FIG. 14, having one stabilizer 12, an end cap 120, and one rigid connector 160. The end coupling 164 has teeth 166 protruding from one end, and notches 167 between the teeth. When the rigid connector 160 is attached to the stabilizer 12, the teeth 166 of the end coupling 164 fit into the notches 114 of the end coupling 28. Simultaneously, the teeth 112 of the end coupling 28 fit into the notches 167 of the end coupling 164. The stabilizer 12 and the rigid connector 160 are rotated in opposite directions so that the teeth 112, 166 interlock and the stabilizer 112 and the rigid connector 160 are locked together. The end cap 120 is interlocked onto the remaining open coupling 28 of the stabilizer 12 as previously described. FIG. 16 depicts one stabilizer 12 interlocked with a rigid connector 160 and an end cap 120, and in a position with components 24, 25 being articulated to allow the assembly to approximate a curve.

Thus, like the above described systems, dynamic stabilization across one level and posterior immobilization and/or fusion across the adjacent level may be accomplished while simultaneously following the desired curvature of the spine. In some cases, it may be desirable to allow immobilization and/or fusion across one level, and dynamic stabilization across the adjacent level on each end. In such a case, a rigid connector 160 with an end coupling 164 at each end could be used, allowing a stabilization module 12 to couple to each end of the rigid connector 160.

Figure 17:
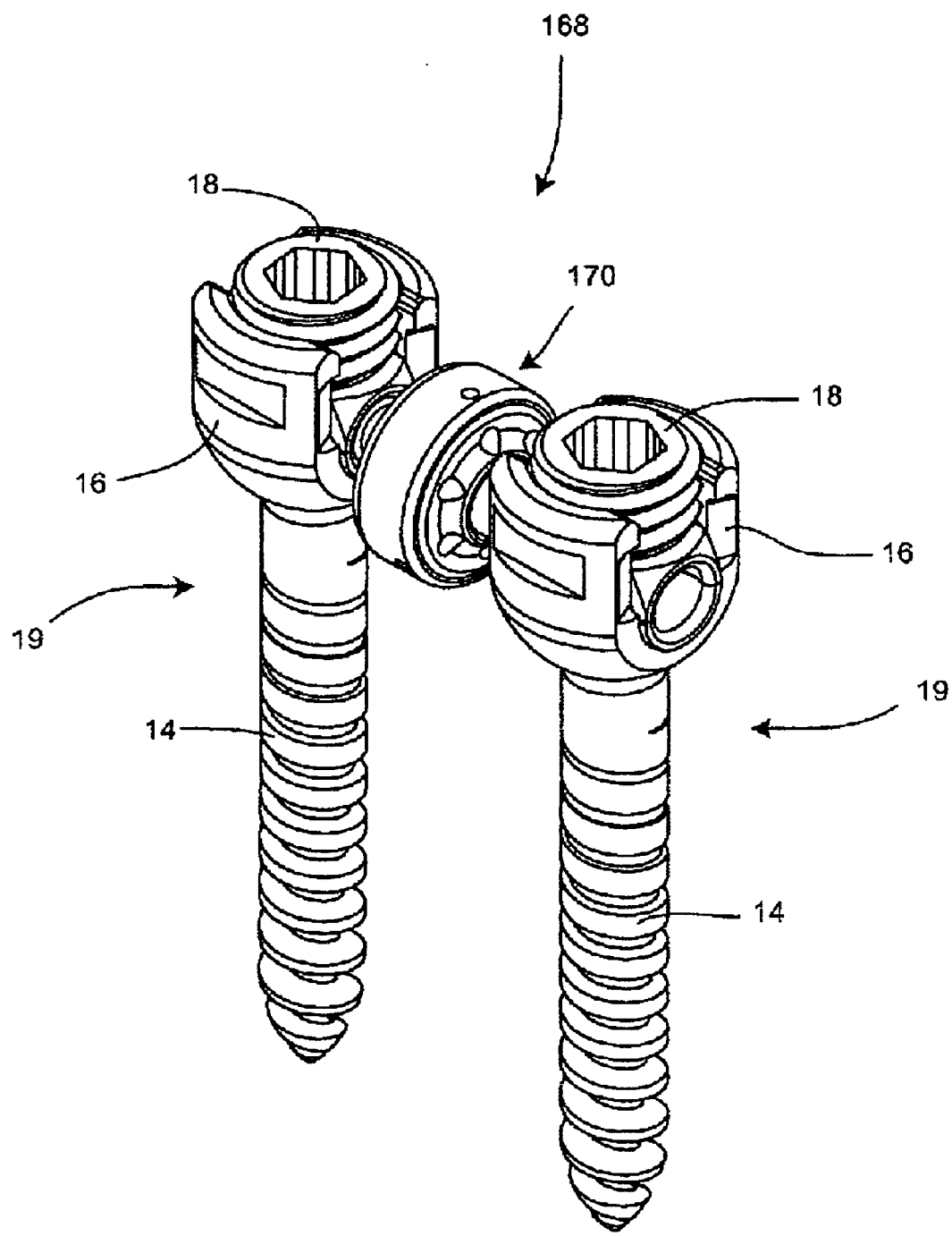
FIG. 17 is a perspective view of another dynamic stabilization assembly according to an alternative embodiment of the invention.

Referring to FIG. 17, an alternative embodiment of a stabilization system 168 is depicted. In this system, a stabilizer 170 is secured to two anchoring members 19. As in the previous embodiment, the anchoring members 19 each preferably include two yokes 16 connected with two fixation members 14, and two set screws 18 are preferably used to hold the stabilizer 170 in place.

Figure 18:
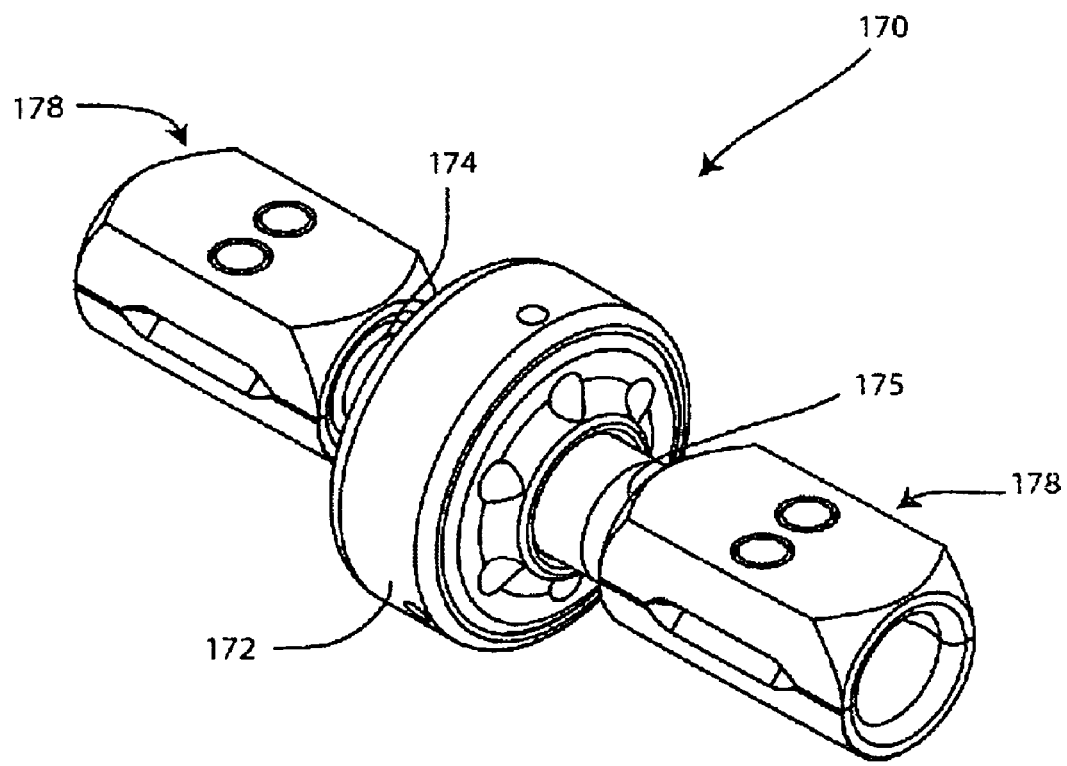
FIG. 18 is an enlarged perspective view of a stabilizer and end couplings of the dynamic stabilization assembly of FIG. 17.
Figure 19:
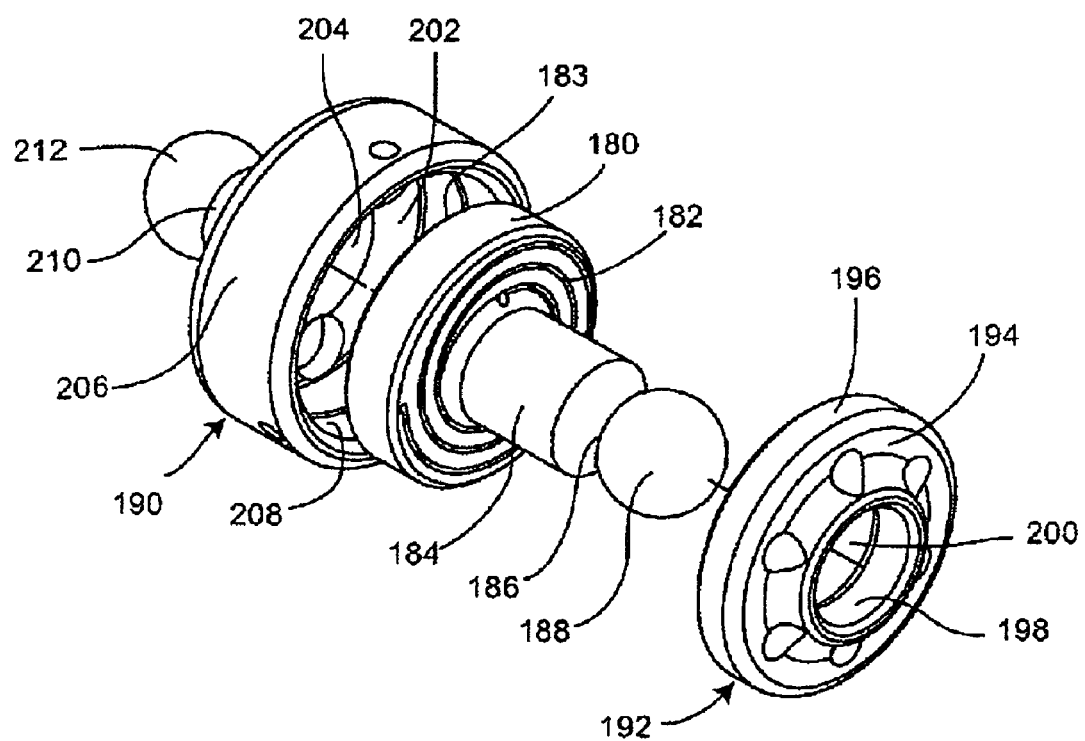
FIG. 19 is an exploded perspective view of the stabilizer of FIG. 18.

As seen in FIG. 18, the stabilizer 170 has a spring casing 172 and two articulation components 174, 175. A two-piece end housing 178 also preferably extends from either articulation component 174, 175. As shown in FIG. 19, the spring casing 172 preferably houses a planar spring 180. The planar spring 180 has a first side 182 and a second side 183. Extending from the first side 182 is an arm 184 which narrows into a neck 186 and terminates in a semispherical surface 188. The spring casing 172 has an outer hollow member 190 and an inner hollow member 192. The inner hollow member 192 is of a shallow dish shape, and has a circular plate 194 which forms the base of the hollow member, with a threaded outer rim 196 which encircles the outside of the plate 194. An inner rim 198 encircles a round hole 200 in the center of the plate 194.

Similarly, the outer hollow member 190 is of a deep dish shape with an interior cavity 202. It has a circular plate 204 which forms the base of the hollow member, and a support member 206 which forms the side wall of the hollow member. An inner surface 208 of the support member 206 is threaded, but a neck 210 extends from the outside of the plate 204 and terminates in a semispherical surface 212. This latter element is different from both inner hollow member 192 and that which is included in the above described embodiments of the present invention.

When assembled, the planar spring 180 preferably fits into the cavity 202 of the outer hollow member 190, with the second side 183 adjacent to the plate 204 of the hollow member 190. The inner hollow member 192 fits over the planar spring 180, so that the arm 184 and the semispherical surface 188 extend through the hole 200 in the inner hollow member 192. Thereafter, the threads on the outer rim 196 engage with the threads on the inner surface 208 of the outer hollow member 190, joining the hollow members 190, 192 to form the casing 172. The spring 180 is thusly captured inside the casing 172, which prevents it from moving axially. When the arm 184 moves toward or away from the outer hollow member 190, the planar spring 180 extends out of its plane. When the arm 184 returns to its original position, the planar spring 180 recoils back towards its plane. During this extension and recoiling, the plate 194 of the inner hollow member 192 and the plate 204 of the outer hollow member 190 act as barriers to limit the movement of the planar spring 180. The arm 184 is encircled by the inner rim 198, which acts as a bearing surface to prevent radial movement of the arm relative to the inferior hollow member 192.

Figure 20:
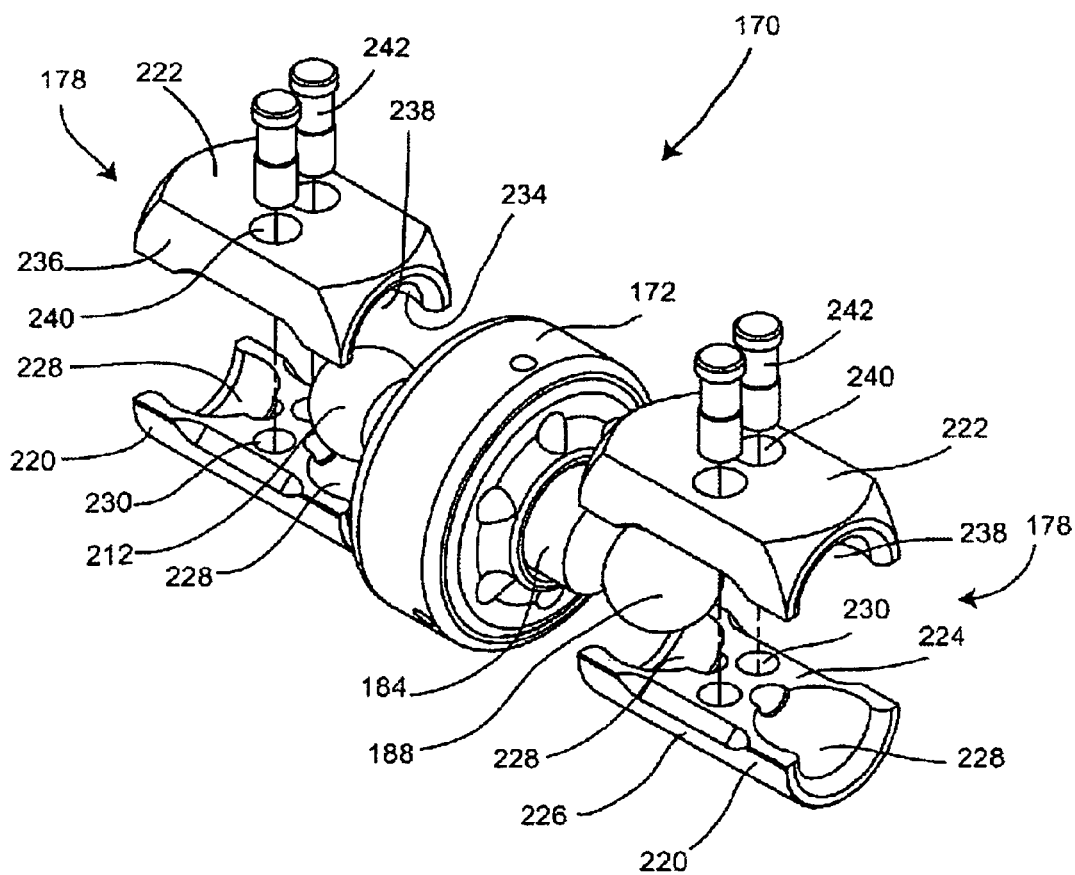
FIG. 20 is an exploded perspective view of the stabilizer and end couplings of FIG. 18.

As seen in FIG. 20, a coupling in the form of a two-part end housing 178 fits over each semispherical surface 188, 212. Each end housing 178 has a first wall 220 and a second wall 222. The first wall 220 is shaped like a segment of a cylindrical body that is split lengthwise, and has an inner surface 224 and rounded outer surface 226. At each lengthwise end of the first wall 220, a rounded first hollow 228 is indented into the inner surface 224. Indented into the inner surface 224, between the hollows 228, are two receiving holes 230. The second wall 222 is also shaped like a segment of a cylindrical body and has an inner surface 234 and an outer surface 236. Unlike the first wall 220, the outer surface 236 is not rounded but is squared off so it is flat. The inner surface 234 has a rounded second hollow 238 indented into each lengthwise end. Each pair of rounded hollows 228, 238 cooperates to define a socket sized to receive the corresponding ball 188 or 212. Two pin holes 240 extend from the outer surface 236 through the wall 222 to the inner surface 234, such that two pins 242 can fit through the pin holes 240 and into the receiving holes 230 in the first wall 220. The pins 242 and receiving holes 230 releasably hold the walls 220, 222 together around the semispherical surfaces 188, 212, and prevent shearing of the walls. In other embodiments of the invention, the pins 242 and receiving holes 230 could be replaced by posts and brackets, or a snap mechanism or other mechanisms capable of releasably joining the walls 220, 222.

Figure 21:
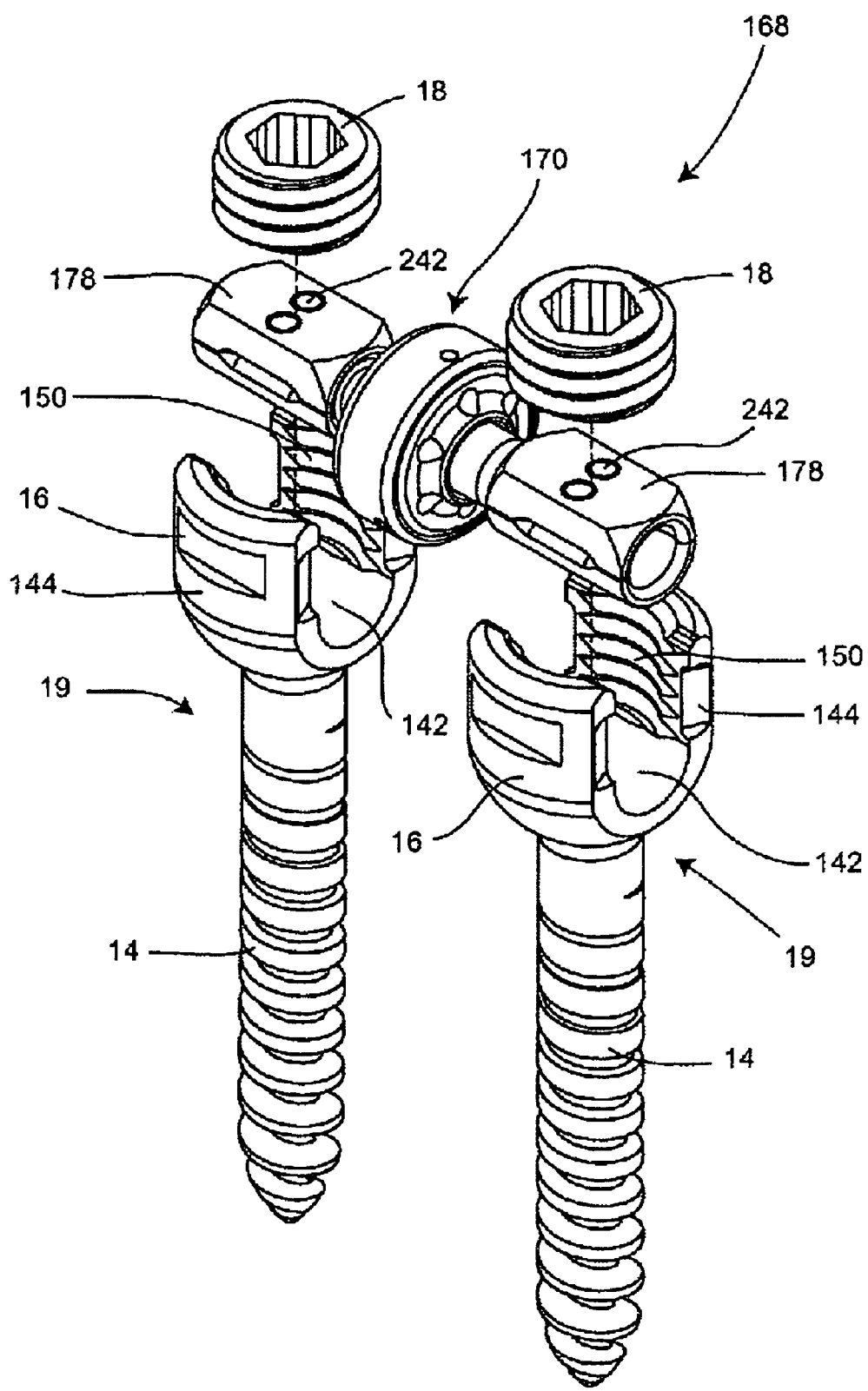
FIG. 21 is a partially exploded perspective view of the dynamic stabilization assembly of FIG. 17.

The assembled stabilizer 170 fits into the yokes 16 of two anchoring members 19, as is best shown in FIG. 17 (shown disassembled in FIG. 21). In the fully assembled state, the end housings 178 are preferably situated perpendicular to the fixation members 14, so that the end housings 178 fit between support walls 144 of anchoring member 19, and the rounded outer surface 226 is cradled on a curved floor 142 between walls 144. Two set screws 18 are thereafter engaged in the threads 150 and tightened. The tightening of the set screws 18 creates pressure on the end housings 178, holding the housings closed around the semispherical surfaces 188, 212. As described in the previous embodiment, each anchoring member 19 may comprise a unitary piece which includes both the fixation member 14 and the yoke 16, or the fixation member 14 and the yoke 16 may be separate pieces. In such an embodiment where the fixation member 14 and yokes 16 are separate pieces, tightening of the set screws 18 may also press the end housings 178 against the heads 142 of the fixation members 14, thereby restricting further rotation of the yokes 16 with respect to the fixation members 14 to secure the entire assembly.

Like the above embodiment, two stabilizers 170 can be secured end-to-end in accordance with this latter embodiment. When two stabilizers 170 are to be used together, the stabilizers are partially assembled as shown in FIG. 19 and described previously. The semispherical surface 212 or 188 from one stabilizer 170 is preferably placed in the empty hollow 228 of the first wall 220 of the second stabilizer 170 before the second wall 222 is joined to the first wall 220. When the second wall 222 is joined to the first wall 220, the semispherical surfaces 212, 188 are captured in the socket sections 228, 238 and the modules are joined. A stabilizer 170 can also be employed in combination with a rigid connector to provide dynamic stabilization across one level and posterior fusion across the adjacent level. Additional levels may be added as desired. Multiple stabilization/fusion levels can include two or more sequential rigid connectors, or rigid connecters sequentially interspersed with stabilizers.

Figure 22:
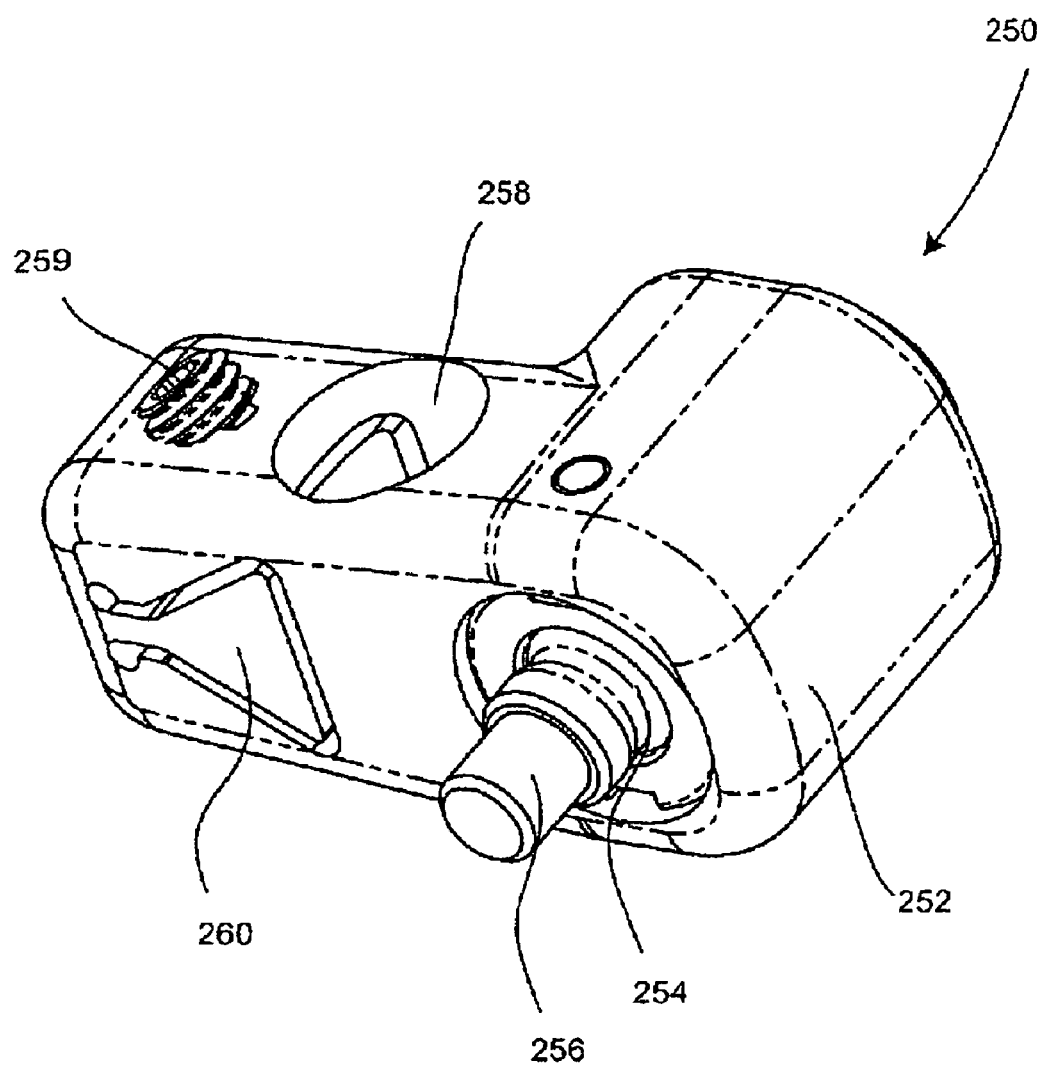
FIG. 22 is a perspective view of an overhung stabilizer and articulating component of an overhung dynamic stabilization assembly designed for shorter pedicle-to-pedicle displacements.

Referring to FIG. 22, a portion of an "overhung" dynamic stabilization system is shown. This system can be used when an offset between adjacent fixation members is desired and/or when a short pedicle-to-pedicle displacement must be accommodated. In this embodiment, a stabilizer 250 includes a housing 252, an articulation component 254 and an arm 256 which extends from the joint. A tunnel 258 provides an opening for placement of the stabilizer 250 over an anchoring member (best shown in FIG. 26), and two set screws 259 are used to press a flexible stop 260 against the anchoring member, securing the stabilizer 250 in place.

Figure 23:
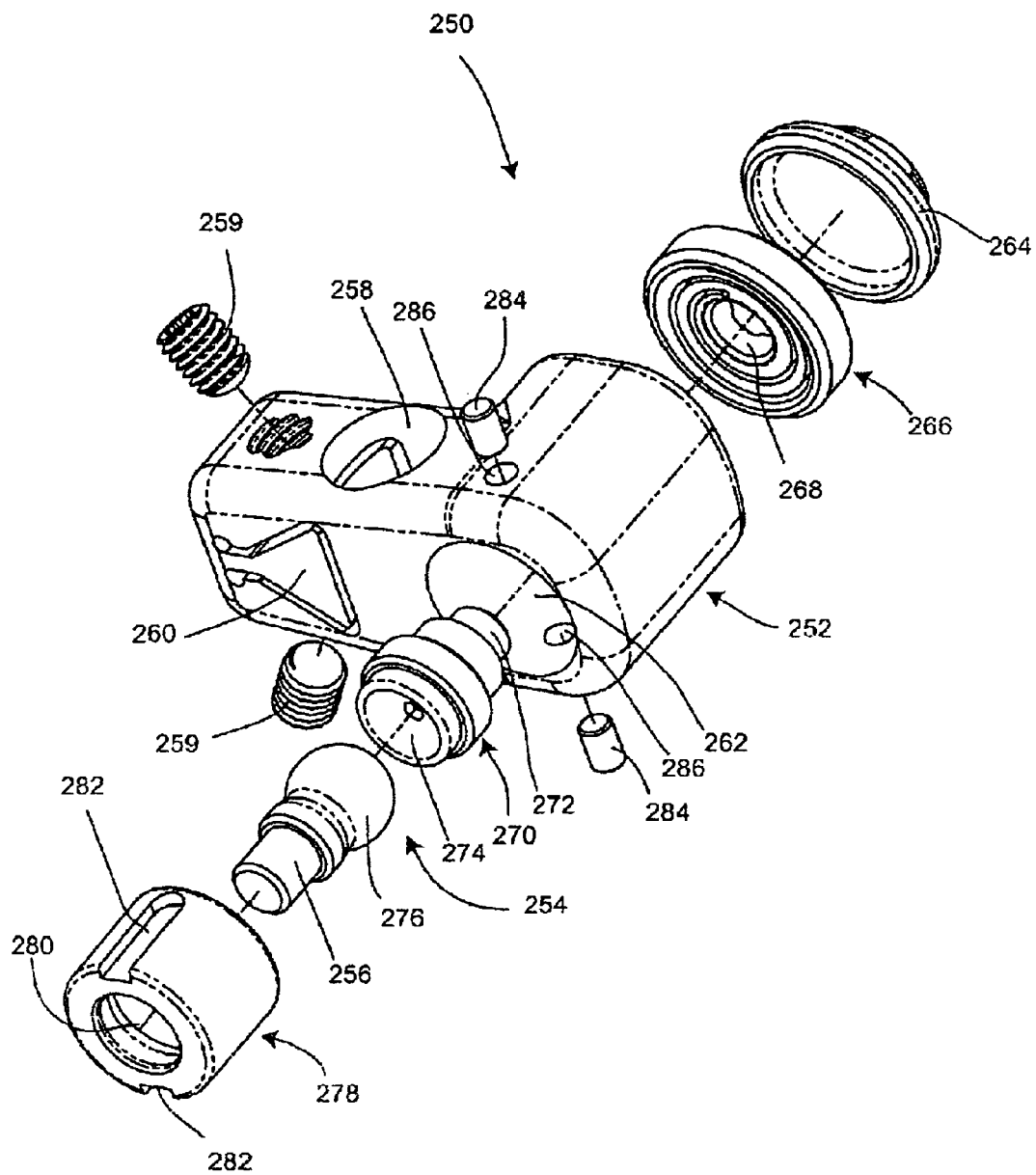
FIG. 23 is an exploded perspective view of the overhung stabilizer of FIG. 22.

FIG. 23 depicts an exploded view of the stabilizer 250 in more detail. As shown in that figure, the housing 252 has a chamber 262 which holds the articulation component 254. A threaded cap 264 is screwed into the housing 252 closing off one end of the chamber 262. A planar spring 266 with a threaded inner ring 268 is positioned within the cap 264. Releasably screwed to the inner ring 268 is a socket 270 with a threaded end stud 272. A cup 274 terminates the socket 270 at the end opposite the threaded end stud 272. A semispherical surface 276 is connected to the arm 256, and the semispherical surface 276 rotatably rests in the cup 274. A tubular sleeve 278 surrounds the socket 270, semispherical surface 276 and arm 256. The sleeve 278 has a central bore 280 through which the arm 256 protrudes. The sleeve 278 also has two grooves 282 which run lengthwise down opposite outer sides of the sleeve. When the sleeve 278, along with the enclosed socket 270, semispherical surface 276 and arm 256 are in the chamber 262, the sleeve is held in place by two pins 284. The pins 284 are inserted through two pin holes 286 which perforate the outer wall of the housing 252. The inserted pins 284 fit into the grooves 282, and prevent the sleeve 278 and its enclosed contents from moving axially.

Figure 24:
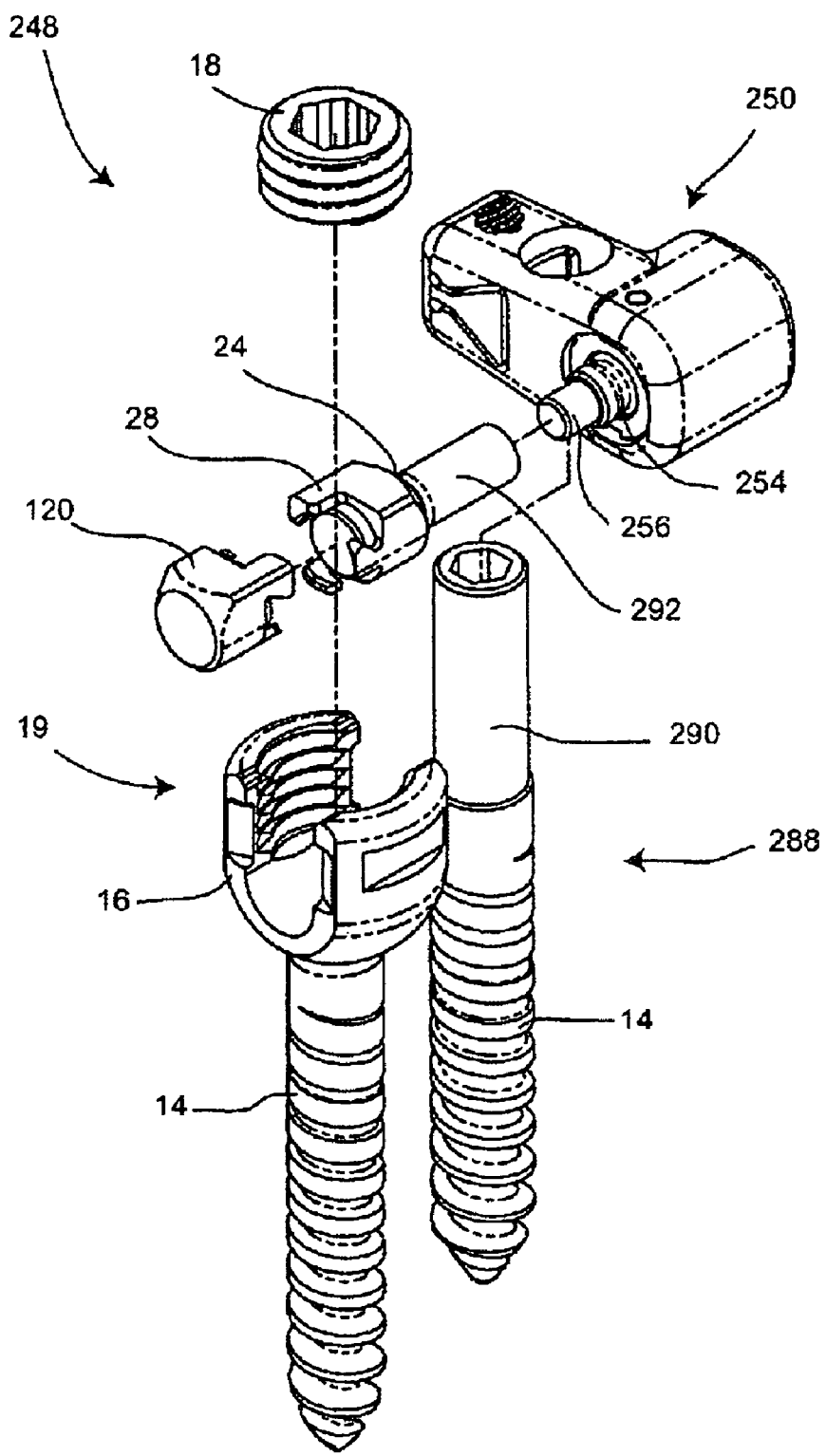
FIG. 24 is a partially exploded perspective view of an overhung dynamic stabilization assembly including the components of FIG. 22.

An unassembled stabilization system 248 is shown in FIG. 24. The system 248 includes the overhung stabilizer 250, an anchoring member 19, an anchoring member 288, an articulation component 24, an end coupling 28 and an end cap 120. As described in previous embodiments, the anchoring member 19 has a fixation member 14, a yoke 16 and a set screw 18. The anchoring member 288 comprises a fixation member 14 and an extension post 290. Once again, the fixation members 14 may comprise pedicle screws, screws fixed to other parts of the vertebrae, pins, clips, clamps, adhesive members, or any other device capable of anchoring the stabilizer to the vertebrae. Additionally, each yoke 16 may be unitarily formed with a fixation member 14 as illustrated herein, or each yoke 16 may be a separate entity and be polyaxially securable to a fixation member 14. The articulation component 24 has a tubular joining arm 292 extending from an end coupling 28. The joining arm 292 is shaped to fit over the end of the arm 256 which protrudes from the articulation component 254.

Figure 25:
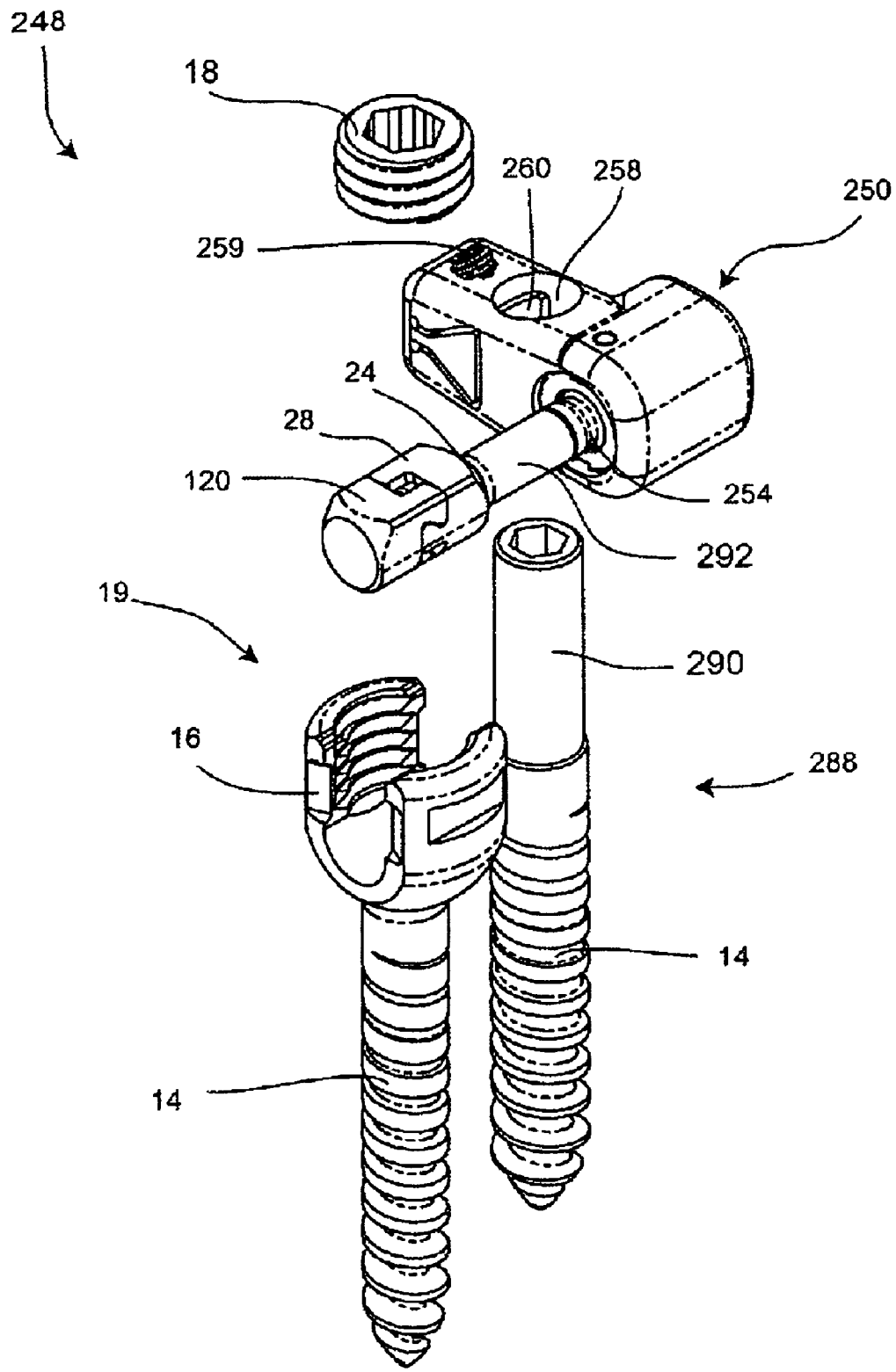
FIG. 25 is another partially exploded perspective view of the overhung dynamic stabilization assembly of FIG. 24.
Figure 26:
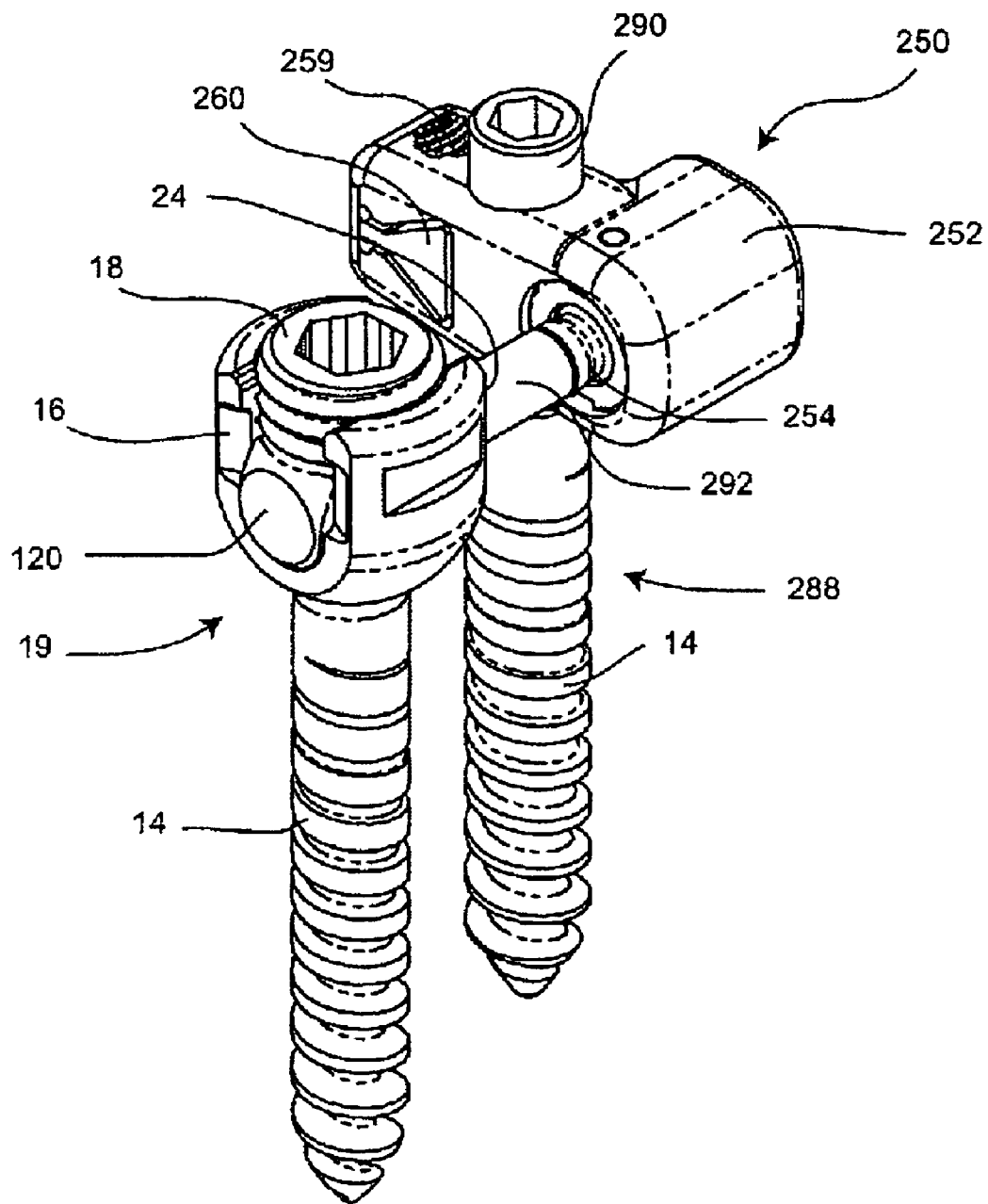
FIG. 26 is a perspective view of a fully assembled overhung dynamic stabilization assembly of FIG. 24.

FIG. 25 illustrates the stabilization system 248 in a partially assembled state. The stabilizer 250 is joined to the articulation component 24 and end coupling 28, with the joining arm 292 fitting over the end of the arm 256 which protrudes from the articulation component 254 through the use of a press fit or other attachment mechanism. The end cap 120 fits on the opposite end of the end coupling 28, in the manner previously described. The fully assembled stabilization system 248 is shown in FIG. 26. In this assembly, the end coupling 28 and end cap 120 fit in the yoke 16 of the anchoring member 19, and are held in place by tightening the set screw 18, in the same manner set forth previously. The assembled stabilizer 250 is placed over the anchoring member 288, with the extension post 290 on the anchoring member 288 extending posteriorly through the tunnel 258. The set screws 259 are engaged in the outer wall of the housing 252 adjacent to the extension post 290. When the set screws 259 are tightened, they push against the flexible stop 260, which in turn pushes against the post 290, holding the stabilizer 250 in place on the extension post 290. Finally, the joining arm 292 connects the articulation component 24 to the articulation component 254, thus pivotably connecting the stabilizer 250, secured to the anchoring member 288, to the anchoring member 19.

When the system 248 is fully assembled and anchored to two adjacent vertebrae, motion between the two vertebrae can cause the planar spring 266 to flex out of its plane. Referring back to FIG. 23, when the two adjacent vertebrae move closer together and the distance between them shortens, the planar spring 266 returns to its plane. When the two adjacent vertebrae move apart and the distance between them lengthens, the planar spring 266 flexes in the opposite direction along the spiral path, toward the sleeve 278. As the planar spring 266 flexes, the sleeve 278 which holds the articulation component 254 slides along the chamber 262. The grooves 282 allow the sleeve 278 to slide back and forth past the pins 284, but the pins 284 restrict axial movement of the sleeve 278 and serve as stops to prevent the sleeve 278 from moving completely out of the chamber 262.

Figure 27:
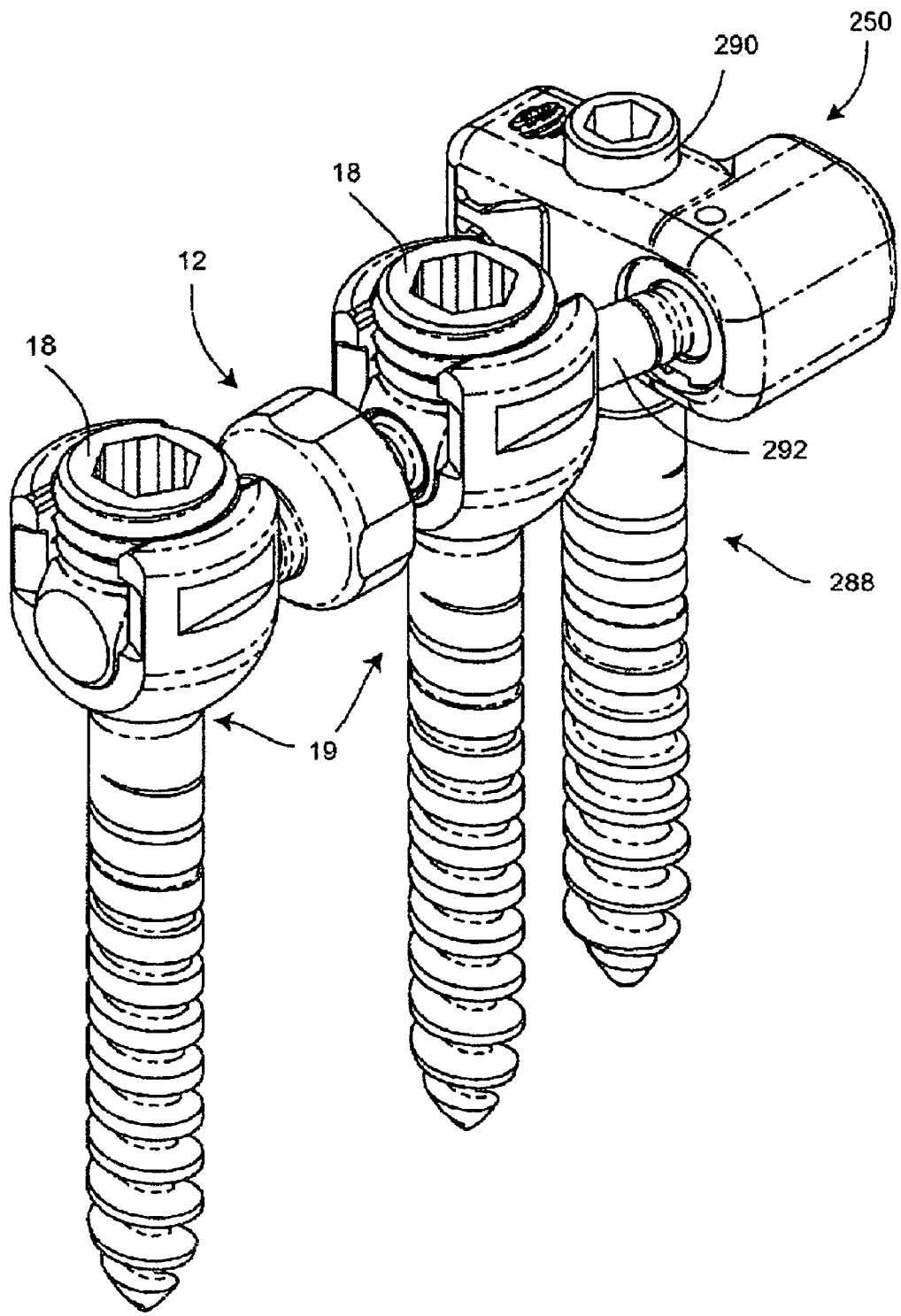
FIG. 27 is a perspective view of the dynamic stabilization assembly including the stabilizer of FIG. 22, along with the overhung stabilization assembly of FIG. 24.
Figure 28:
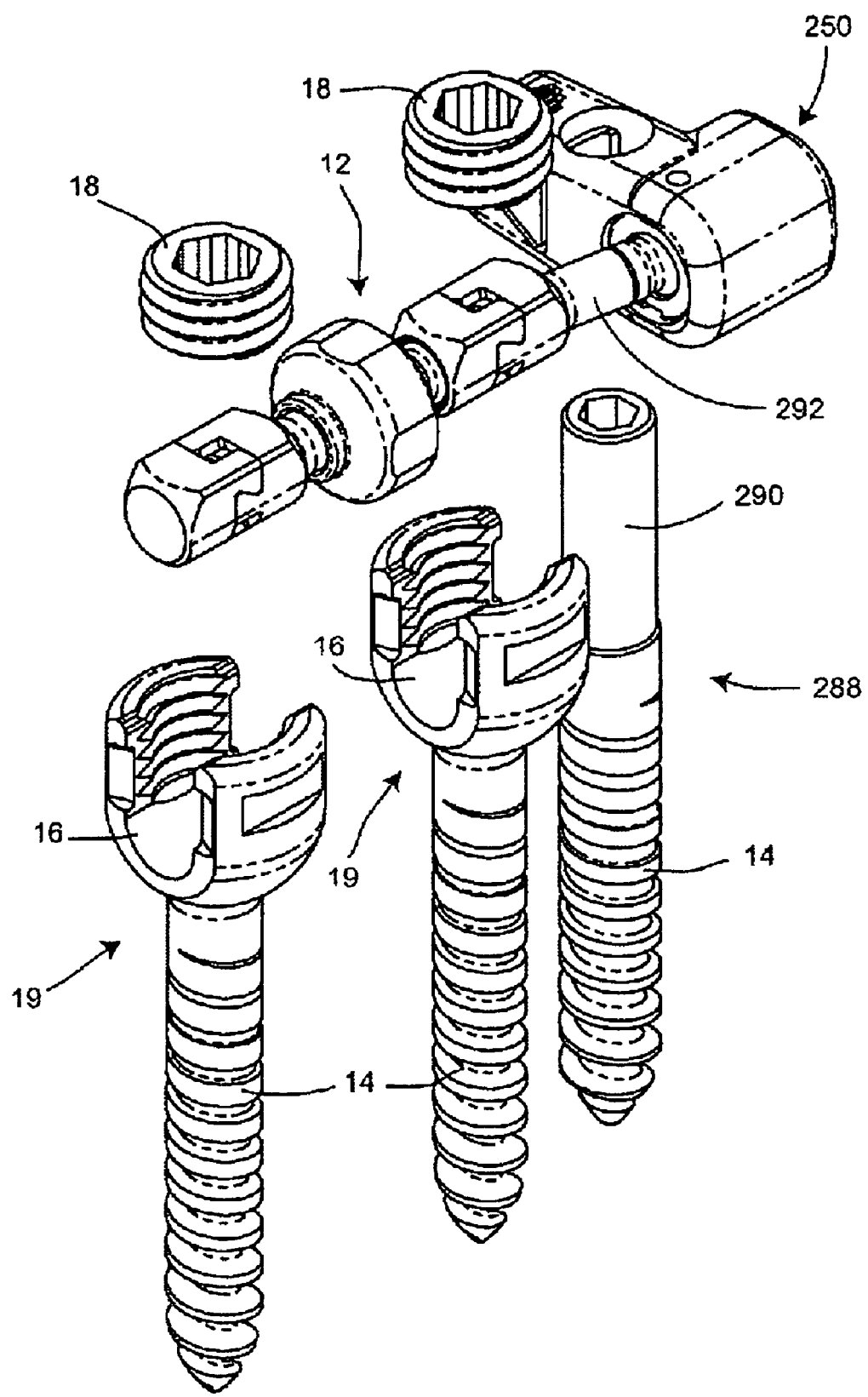
FIG. 28 is an exploded perspective view of the dynamic stabilization assembly of FIG. 27.

Referring to FIG. 27, a multi-level dynamic stabilization system is shown which includes a stabilizer 12 as per FIGS. 1-8, and an overhung stabilizer 250 as per FIGS. 22-26. The stabilizer 12 is mounted on two anchoring members 19 and connected via the joining arm 292 to the overhung stabilizer 250 which is mounted an anchoring member 288. The resulting dynamic stabilization system provides stabilization across two adjacent vertebral levels. The overhung stabilizer 250 allows one of the levels to have a relatively short pedicle-to-pedicle displacement. FIG. 28 illustrates the stabilizers 12, 250, two anchoring members 19 and one anchoring member 288 in an exploded view. Each anchoring members 19 includes a fixation member 14, a yoke 16 and a set screw 18, as set forth previously. The anchoring member 288 includes a fixation member 14 with an extension post 290, as set forth previously.

Figure 29:
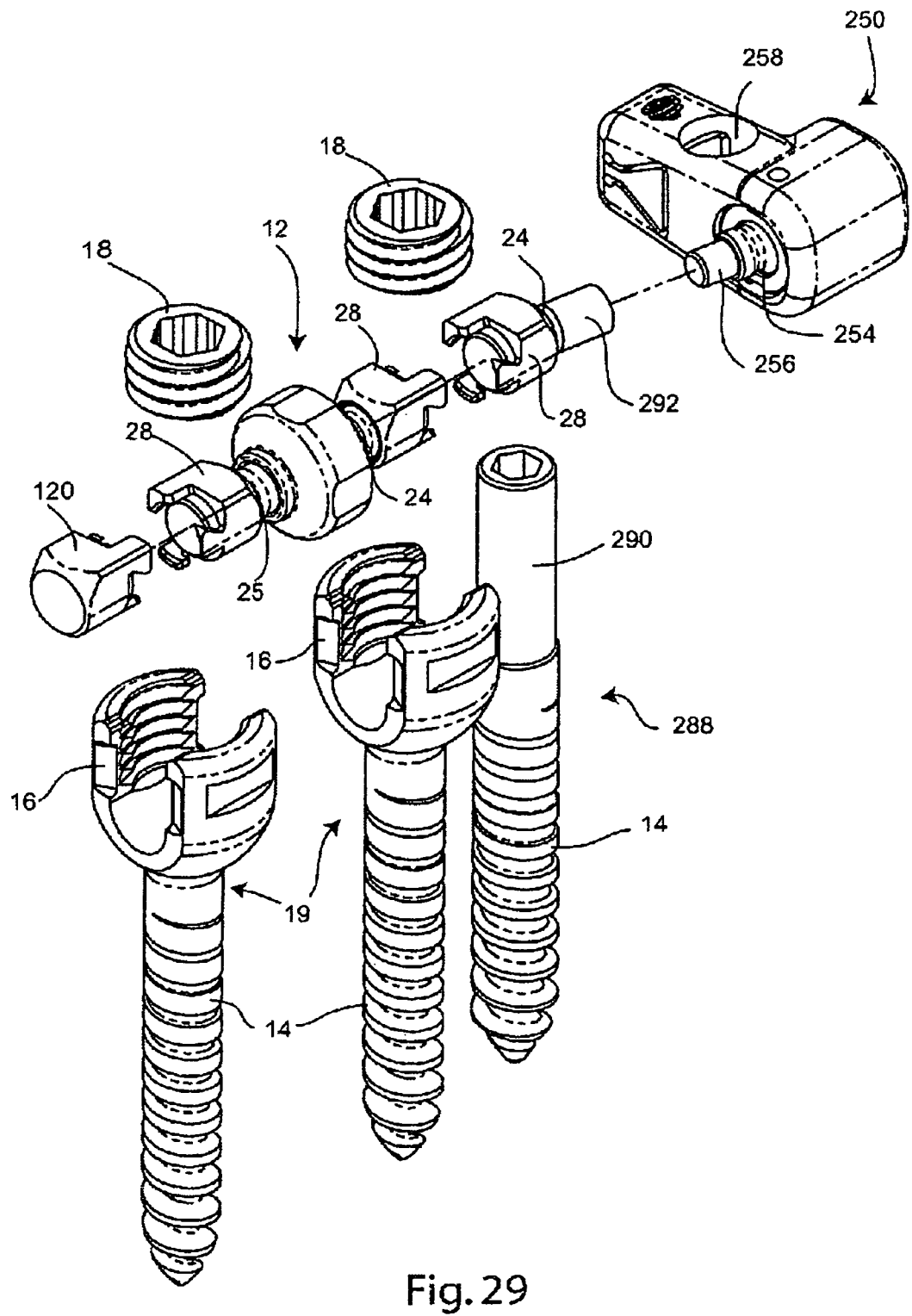
FIG. 29 is a further exploded perspective view of the dynamic stabilization assembly of FIG. 27.

Referring to FIG. 29, the stabilizers 12, 250 and the anchoring members 19, 288 are shown in a further exploded view. The stabilizer 12 has two end couplings 28, one end coupling 28 connecting with one end cap 120 thereby forming a coupling mountable in a yoke 16. The second end coupling 28 of the stabilizer 12 preferably couples with the end coupling 28 that connects to the joining arm 292, forming a coupling mountable in another yoke 16. The joining arm 292 fits over the arm 256 of the stabilizer 250, thus connecting the stabilizer 250 to the stabilizer 12. The stabilizer 250 is mountable on the anchoring member 288, in the manner set forth previously. When assembled, this two level system has two articulation components 24, one articulation component 25, and one articulation component 254, providing pivotability between the stabilized vertebrae. Additionally, an overhung stabilizer 250, a stabilizer 12, and/or a stabilizer 170 such as that depicted in FIGS. 17-21 can be implanted in combination with a rigid connector 160 such as that depicted in FIGS. 14-16.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for controlling relative motion between a first vertebra and a second vertebra, the method comprising:
    positioning a planar spring of a first stabilizer;
    attaching a first coupling of the first stabilizer to the first vertebra; and
    attaching a second coupling of the first stabilizer to the second vertebra;
    wherein, after attachment of the couplings to the vertebrae, the planar spring is positioned to transmit resilient force between the vertebrae via flexure of at least a portion of the planar spring out-of-plane, the planar spring being predisposed to resist such flexion out-of-plane, and
    wherein the planar spring is configured to flex out-of-plane in a first direction in response to movement of the vertebrae towards one another and out-of-plane in a second opposing direction in response to movement of the vertebrae away from one another, the planar spring being predisposed to resist such flexion out-of-plane.

2. The method of claim 1, wherein the first stabilizer comprises a casing comprising a hollow first member and a hollow second member, wherein the planar spring is positioned within a cavity defined by engagement of the first and second hollow members, wherein the hollow members limit relative motion of the vertebrae by limiting deflection of the planar spring.

3. The method of claim 1, wherein, after attachment of the couplings to the vertebrae, the planar spring is able to urge the first and second vertebrae to move closer together and further apart.

4. The method of claim 1, wherein attaching the first coupling to the first vertebra includes attaching the first coupling to a yoke of a first anchoring member and implanting a fixation member of the first anchoring member in a pedicle of the first vertebra, and attaching the second coupling to the second vertebra includes attaching the second coupling to a yoke of a second anchoring member and implanting a fixation member of the second anchoring member in a pedicle of the second vertebra, wherein each yoke is polyaxially coupled to the corresponding fixation member.

5. The method of claim 1, wherein a path followed by the planar spring is generally spiral-shaped, and the planar spring comprises a central portion attached to the first coupling and a peripheral portion attached to the second coupling.

6. The method of claim 1, wherein the first stabilizer further comprises a first articulation component, wherein articulating the first articulation component permits polyaxial relative rotation between the stabilizer and one of the first or second couplings, wherein the first articulation component comprises a semispherical surface and a socket within which the semispherical surface is rotatable.

7. The method of claim 1, wherein attaching the first coupling to the first vertebra comprises securing a first anchoring member to the first vertebra and attaching the first coupling to the first anchoring member, the method further comprising attaching a third coupling of a second component to the first anchoring member such that the first anchoring member simultaneously retains the first and third couplings.

8. The method of claim 7, wherein the second component comprises a rigid connector further comprising a fourth coupling, wherein the third .and fourth couplings are substantially rigidly connected together.

9. The method of claim 7, wherein the second component comprises a second stabilizer further comprising a fourth coupling and a second resilient member, wherein the second resilient member exerts resilient force between the third and fourth couplings.

10. A method for controlling relative motion between a first vertebra and a second vertebra, the method comprising:
    selecting a component selected from the group consisting of a first stabilizer and a first rigid connector;
    wherein the first stabilizer comprises a first coupling, a second coupling adapted to be attached to a second anchoring member secured to the second vertebra, a resilient member configured to transmit resilient force between the first and second couplings, and a first articulation component configured to articulate to permit relative rotation between the first and second couplings;
    wherein the first rigid connector comprises a first coupling and a second coupling substantially rigidly connected to the first coupling and the resilient member includes a planar spring, at least a portion of which flexes out-of-plane, the planar spring being predisposed to resist such flexion out-of-plane;
    attaching a first coupling of the selected component to a first anchoring member secured to the first vertebra; and
    attaching a second coupling of the selected component to a second anchoring member secured to the second vertebra,
    wherein the planar spring is configured to flex out-of-plane in a first direction in response to movement of the first and second vertebrae towards one another and out-of-plane in a second opposing direction in response to movement of the first and second vertebrae away from one another.

11. The method of claim 10, wherein attaching the first coupling to the first vertebra includes attaching the first coupling to a yoke of the first anchoring member and implanting a fixation member of the first anchoring member in a pedicle of the first vertebra, and attaching the second coupling to the second vertebra comprises attaching the second coupling to a yoke of the second anchoring member and implanting a fixation member of the second anchoring member in a pedicle of the second vertebra, wherein each yoke is polyaxially coupled to the corresponding fixation member.

12. The method of claim 10, wherein the first stabilizer further includes a casing including a hollow first member and a hollow second member, wherein the resilient member is positioned within a cavity defined by engagement of the first and second hollow members.

13. The method of claim 10, wherein the first articulation component comprises a semispherical surface and a socket within which the semispherical surface is rotatable to permit polyaxial motion between the resilient member and the first anchoring member.

14. The method of claim 10, wherein, after attachment of the couplings to the vertebrae, the resilient member is able to urge the first and second vertebrae to move closer together and further apart.

15. The method of claim 10, further comprising attaching a fifth coupling of a second component to the first anchoring member such that the first anchoring member simultaneously retains the first and fifth couplings.

* * * * *

UNITED STATES PATENT AND TRADEMARK OFFICE
CERTIFICATE OF CORRECTION

| | |
|---|---|
| PATENT NO. | : 8,109,973 B2 |
| APPLICATION NO. | : 11/589512 |
| DATED | : February 7, 2012 |
| INVENTOR(S) | : Daniel E. Gerbec et al. |

It is certified that error appears in the above-identified patent and that said Letters Patent is hereby corrected as shown below:

In the Claims

Column 13, line 35, after "out-of-plane," delete "the planar spring being predisposed to resist such flexion out-of-plane,".

Signed and Sealed this
Eleventh Day of August, 2015

Michelle K. Lee
*Director of the United States Patent and Trademark Office*